US010568559B2

(12) United States Patent
Parker et al.

(10) Patent No.: US 10,568,559 B2
(45) Date of Patent: Feb. 25, 2020

(54) METHOD AND APPARATUS FOR MEASUREMENT OF NEURAL RESPONSE

(75) Inventors: John Louis Parker, Artarmon (AU); Dean Michael Karantonis, Artarmon (AU)

(73) Assignee: Saluda Medical Pty Ltd, Artarmon (AU)

(*) Notice: Subject to any disclaimer, the term of this patent is extended or adjusted under 35 U.S.C. 154(b) by 0 days.

(21) Appl. No.: 14/117,140

(22) PCT Filed: May 11, 2012

(86) PCT No.: PCT/AU2012/000513
§ 371 (c)(1),
(2), (4) Date: Nov. 12, 2013

(87) PCT Pub. No.: WO2012/155185
PCT Pub. Date: Nov. 22, 2012

(65) Prior Publication Data
US 2014/0296737 A1    Oct. 2, 2014

(30) Foreign Application Priority Data

May 13, 2011 (AU) ................................ 2011901817
May 13, 2011 (AU) ................................ 2011901826

(51) Int. Cl.
*A61B 5/00* (2006.01)
*A61N 1/36* (2006.01)
*A61B 18/14* (2006.01)

(52) U.S. Cl.
CPC .............. *A61B 5/40* (2013.01); *A61B 5/4893* (2013.01); *A61B 18/14* (2013.01); *A61N 1/36185* (2013.01)

(58) Field of Classification Search
CPC .............. A61N 1/36071; A61N 1/0551; A61B 5/04001; A61B 5/4041
See application file for complete search history.

(56) References Cited

U.S. PATENT DOCUMENTS 3,736,434 A    5/1973   Darrow
3,817,254 A    6/1974   Maurer
(Continued)

FOREIGN PATENT DOCUMENTS

EP          0219084       4/1987
EP          0998958 B1    8/2005
(Continued)

OTHER PUBLICATIONS

Yuan S. et al.; Recording monophasic action potentials using a platinum-electrode ablation catheter. Europace. Oct. 2000; 2(4):312-9; Abstract.*

(Continued)

Primary Examiner — Patrick Fernandes
(74) Attorney, Agent, or Firm — KPPB LLP

(57) ABSTRACT

A method for determining a desired location at which to apply a neural therapy. An array of electrodes is positioned proximal to neural tissue. A stimulus is applied from the array which evokes a neural compound action potential response in the neural tissue proximal to the array. A plurality of electrodes of the array simultaneously obtain respective measurements of the neural compound action potential response. From the measurements of the neural compound action potential response a desired location for a neural therapy is determined.

18 Claims, 8 Drawing Sheets

(56) References Cited

U.S. PATENT DOCUMENTS

| | | |
|---|---|---|
| 3,898,472 A | 8/1975 | Long |
| 4,158,196 A | 6/1979 | Crawford, Jr. |
| 4,418,695 A | 12/1983 | Buffet |
| 4,474,186 A | 10/1984 | Ledley et al. |
| 4,628,934 A | 12/1986 | Pohndorf et al. |
| 4,807,643 A | 2/1989 | Rosier |
| 4,856,525 A | 8/1989 | Van Den et al. |
| 5,113,859 A | 5/1992 | Funke |
| 5,139,020 A | 8/1992 | Koestner et al. |
| 5,143,081 A | 9/1992 | Young et al. |
| 5,156,154 A | 10/1992 | Valenta, Jr. et al. |
| 5,172,690 A | 12/1992 | Nappholz et al. |
| 5,184,615 A | 2/1993 | Nappholz et al. |
| 5,188,106 A | 2/1993 | Nappholz et al. |
| 5,215,100 A | 6/1993 | Spitz |
| 5,324,311 A | 6/1994 | Acken |
| 5,417,719 A | 5/1995 | Hull et al. |
| 5,431,693 A | 7/1995 | Schroeppel |
| 5,458,623 A | 10/1995 | Lu et al. |
| 5,476,486 A | 12/1995 | Lu et al. |
| 5,497,781 A | 3/1996 | Chen et al. |
| 5,638,825 A | 6/1997 | Yamazaki et al. |
| 5,702,429 A | 12/1997 | King et al. |
| 5,758,651 A | 6/1998 | Nygard et al. |
| 5,776,170 A | 7/1998 | Macdonald et al. |
| 5,785,651 A | 7/1998 | Kuhn et al. |
| 5,792,212 A | 8/1998 | Weijand et al. |
| 5,814,092 A | 9/1998 | King |
| 5,913,882 A | 6/1999 | King |
| 5,999,848 A | 12/1999 | Gord et al. |
| 6,020,857 A | 2/2000 | Podger |
| 6,027,456 A * | 2/2000 | Feler ............... A61N 1/36021 600/554 |
| 6,038,480 A | 3/2000 | Hrdlicka et al. |
| 6,066,163 A | 5/2000 | John |
| 6,114,164 A | 9/2000 | Dennis et al. |
| 6,144,881 A | 11/2000 | Hemming et al. |
| 6,157,861 A | 12/2000 | Faltys et al. |
| 6,212,431 B1 | 4/2001 | Hahn et al. |
| 6,246,912 B1 | 6/2001 | Sluijter et al. |
| 6,381,496 B1 | 4/2002 | Meadows et al. |
| 6,463,328 B1 | 10/2002 | John |
| 6,473,649 B1 | 10/2002 | Gryzwa et al. |
| 6,473,653 B1 | 10/2002 | Schallhorn et al. |
| 6,493,576 B1 | 12/2002 | Dankwart-Eder |
| 6,522,932 B1 | 2/2003 | Kuzma |
| 6,600,955 B1 | 7/2003 | Zierhofer et al. |
| 6,658,293 B2 | 12/2003 | Vonk et al. |
| 6,675,046 B2 | 1/2004 | Holsheimer |
| 6,782,292 B2 | 8/2004 | Whitehurst |
| 6,898,582 B2 | 5/2005 | Lange |
| 7,089,059 B1 | 8/2006 | Pless |
| 7,171,261 B1 * | 1/2007 | Litvak ............... A61B 5/4041 600/544 |
| 7,231,254 B2 | 6/2007 | DiLorenzo et al. |
| 7,286,876 B2 | 10/2007 | Yonce et al. |
| 7,412,287 B2 | 8/2008 | Yonce et al. |
| 7,450,992 B1 | 11/2008 | Cameron |
| 7,734,340 B2 | 6/2010 | De Ridder |
| 7,742,810 B2 | 6/2010 | Moffitt |
| 7,792,584 B2 | 9/2010 | Van Oort et al. |
| 7,818,052 B2 | 10/2010 | Litvak et al. |
| 7,831,305 B2 | 11/2010 | Gliner |
| 7,835,804 B2 | 11/2010 | Fridman et al. |
| 8,190,251 B2 | 5/2012 | Molnar et al. |
| 8,224,459 B1 | 7/2012 | Pianca et al. |
| 8,239,031 B2 | 8/2012 | Fried et al. |
| 8,359,102 B2 | 1/2013 | Thacker et al. |
| 8,494,645 B2 | 7/2013 | Spitzer et al. |
| 8,588,929 B2 | 11/2013 | Davis et al. |
| 8,670,830 B2 | 3/2014 | Carlson et al. |
| 8,886,323 B2 | 11/2014 | Wu et al. |
| 9,155,892 B2 | 10/2015 | Parker et al. |
| 9,302,112 B2 | 4/2016 | Bornzin et al. |
| 9,381,356 B2 | 7/2016 | Parker et al. |
| 9,386,934 B2 | 7/2016 | Parker et al. |
| 9,974,455 B2 | 5/2018 | Parker et al. |
| 10,206,596 B2 | 2/2019 | Single et al. |
| 10,278,600 B2 | 5/2019 | Parker et al. |
| 10,368,762 B2 | 8/2019 | Single |
| 2002/0055688 A1 | 5/2002 | Katims |
| 2002/0099419 A1 | 7/2002 | Ayal et al. |
| 2002/0193670 A1 | 12/2002 | Garfield et al. |
| 2003/0032889 A1 | 2/2003 | Wells |
| 2003/0045909 A1 | 3/2003 | Gross et al. |
| 2003/0139781 A1 | 7/2003 | Bradley et al. |
| 2003/0195580 A1 | 10/2003 | Bradley et al. |
| 2004/0088017 A1 | 5/2004 | Sharma et al. |
| 2004/0122482 A1 | 6/2004 | Tung et al. |
| 2004/0158298 A1 * | 8/2004 | Gliner ............... A61N 1/0531 607/48 |
| 2004/0225211 A1 | 11/2004 | Gozani et al. |
| 2004/0254494 A1 | 12/2004 | Spokoyny et al. |
| 2005/0010265 A1 | 1/2005 | Baru Fassio |
| 2005/0017190 A1 * | 1/2005 | Eversmann ........ G01N 27/4145 250/370.14 |
| 2005/0021104 A1 | 1/2005 | DiLorenzo |
| 2005/0065427 A1 | 3/2005 | Magill |
| 2005/0070982 A1 | 3/2005 | Heruth et al. |
| 2005/0075683 A1 | 4/2005 | Miesel et al. |
| 2005/0101878 A1 | 5/2005 | Daly |
| 2005/0113877 A1 | 5/2005 | Giardiello et al. |
| 2005/0137670 A1 | 6/2005 | Christopherson et al. |
| 2005/0149154 A1 | 7/2005 | Cohen |
| 2005/0192567 A1 | 9/2005 | Katims |
| 2005/0203600 A1 | 9/2005 | Wallace |
| 2005/0209655 A1 | 9/2005 | Bradley et al. |
| 2005/0282149 A1 | 12/2005 | Kovacs et al. |
| 2006/0009820 A1 | 1/2006 | Royle et al. |
| 2006/0020291 A1 | 1/2006 | Gozani |
| 2006/0135998 A1 | 6/2006 | Libbus et al. |
| 2006/0195159 A1 * | 8/2006 | Bradley ............. A61N 1/36132 607/48 |
| 2006/0212089 A1 | 9/2006 | Tass |
| 2006/0217782 A1 | 9/2006 | Boveja et al. |
| 2006/0264752 A1 | 11/2006 | Rubinsky et al. |
| 2006/0287609 A1 | 12/2006 | Litvak et al. |
| 2007/0021800 A1 | 1/2007 | Bradley et al. |
| 2007/0073354 A1 | 3/2007 | Knudson et al. |
| 2007/0100378 A1 | 5/2007 | Maschino |
| 2007/0178579 A1 | 8/2007 | Ross et al. |
| 2007/0185409 A1 | 8/2007 | Wu et al. |
| 2007/0208394 A1 | 9/2007 | King et al. |
| 2007/0225767 A1 | 9/2007 | Daly |
| 2007/0244410 A1 | 10/2007 | Fridman |
| 2007/0250120 A1 | 10/2007 | Flach et al. |
| 2007/0255372 A1 | 11/2007 | Metzler et al. |
| 2007/0282217 A1 | 12/2007 | McGinnis et al. |
| 2007/0287931 A1 | 12/2007 | Dilorenzo |
| 2008/0021292 A1 | 1/2008 | Stypulkowski |
| 2008/0051647 A1 | 2/2008 | Wu et al. |
| 2008/0064947 A1 | 3/2008 | Heruth et al. |
| 2008/0077191 A1 | 3/2008 | Morrell |
| 2008/0097529 A1 | 4/2008 | Parramon et al. |
| 2008/0147155 A1 | 6/2008 | Swoyer |
| 2008/0183076 A1 * | 7/2008 | Witte ............... A61B 5/0093 600/438 |
| 2008/0208304 A1 | 8/2008 | Zdravkovic et al. |
| 2008/0234780 A1 | 9/2008 | Smith et al. |
| 2008/0275527 A1 | 11/2008 | Greenberg et al. |
| 2008/0294221 A1 | 11/2008 | Kilgore |
| 2008/0300655 A1 | 12/2008 | Cholette et al. |
| 2009/0033486 A1 * | 2/2009 | Costantino ........... A61B 5/1107 340/540 |
| 2009/0082691 A1 | 3/2009 | Denison et al. |
| 2009/0157155 A1 | 6/2009 | Bradley |
| 2009/0270957 A1 | 10/2009 | Pianca |
| 2009/0287277 A1 | 11/2009 | Conn et al. |
| 2009/0299214 A1 | 12/2009 | Wu et al. |
| 2009/0306491 A1 | 12/2009 | Haggers |
| 2010/0010388 A1 | 1/2010 | Panken et al. |
| 2010/0058126 A1 | 3/2010 | Chang et al. |
| 2010/0069835 A1 | 3/2010 | Parker |
| 2010/0069996 A1 | 3/2010 | Strahl |

(56) References Cited

U.S. PATENT DOCUMENTS

| | | |
|---|---|---|
| 2010/0070007 A1 | 3/2010 | Parker |
| 2010/0070008 A1 | 3/2010 | Parker |
| 2010/0106231 A1* | 4/2010 | Torgerson .......... A61N 1/36082 607/116 |
| 2010/0114237 A1 | 5/2010 | Giftakis et al. |
| 2010/0114258 A1 | 5/2010 | Donofrio et al. |
| 2010/0125313 A1 | 5/2010 | Lee et al. |
| 2010/0125314 A1 | 5/2010 | Bradley et al. |
| 2010/0145222 A1 | 6/2010 | Brunnett et al. |
| 2010/0152808 A1 | 6/2010 | Boggs |
| 2010/0179626 A1 | 7/2010 | Pilarski |
| 2010/0191307 A1 | 7/2010 | Fang et al. |
| 2010/0204748 A1 | 8/2010 | Lozano et al. |
| 2010/0222844 A1 | 9/2010 | Troosters et al. |
| 2010/0222858 A1 | 9/2010 | Meloy |
| 2010/0249643 A1 | 9/2010 | Gozani |
| 2010/0249867 A1 | 9/2010 | Wanasek |
| 2010/0258342 A1 | 10/2010 | Parker |
| 2010/0262208 A1 | 10/2010 | Parker |
| 2010/0262214 A1 | 10/2010 | Robinson |
| 2010/0280570 A1 | 11/2010 | Sturm et al. |
| 2010/0286748 A1 | 11/2010 | Midani et al. |
| 2010/0331604 A1 | 12/2010 | Okamoto et al. |
| 2010/0331926 A1 | 12/2010 | Lee et al. |
| 2011/0004207 A1 | 1/2011 | Wallace et al. |
| 2011/0021943 A1 | 1/2011 | Lacour et al. |
| 2011/0028859 A1 | 2/2011 | Chian |
| 2011/0087085 A1 | 4/2011 | Tsampazis et al. |
| 2011/0093042 A1 | 4/2011 | Torgerson et al. |
| 2011/0106100 A1 | 5/2011 | Bischoff |
| 2011/0184488 A1 | 7/2011 | De Ridder et al. |
| 2011/0204811 A1 | 8/2011 | Pollmann-retsch |
| 2011/0224749 A1 | 9/2011 | Ben-David et al. |
| 2011/0264165 A1 | 10/2011 | Molnar et al. |
| 2011/0270343 A1 | 11/2011 | Buschman et al. |
| 2011/0307030 A1 | 12/2011 | John |
| 2011/0313310 A1 | 12/2011 | Tomita |
| 2011/0313483 A1 | 12/2011 | Hincapie et al. |
| 2012/0029377 A1 | 2/2012 | Polak |
| 2012/0101552 A1 | 4/2012 | Lazarewicz et al. |
| 2012/0109236 A1 | 5/2012 | Jacobson et al. |
| 2012/0253423 A1 | 10/2012 | Youn et al. |
| 2012/0277621 A1 | 11/2012 | Gerber et al. |
| 2012/0277823 A1 | 11/2012 | Gerber et al. |
| 2013/0053722 A1 | 2/2013 | Carlson et al. |
| 2013/0060302 A1 | 3/2013 | Polefko et al. |
| 2013/0172774 A1 | 7/2013 | Crowder et al. |
| 2013/0289661 A1 | 10/2013 | Griffith et al. |
| 2013/0289683 A1 | 10/2013 | Parker et al. |
| 2014/0066803 A1 | 3/2014 | Choi |
| 2014/0142447 A1 | 5/2014 | Takahashi et al. |
| 2014/0194771 A1 | 7/2014 | Parker et al. |
| 2014/0194772 A1 | 7/2014 | Single et al. |
| 2014/0236042 A1 | 8/2014 | Parker et al. |
| 2014/0236257 A1 | 8/2014 | Parker et al. |
| 2014/0243926 A1 | 8/2014 | Carcieri |
| 2014/0243931 A1 | 8/2014 | Parker et al. |
| 2014/0276195 A1 | 9/2014 | Papay et al. |
| 2014/0277250 A1 | 9/2014 | Su et al. |
| 2014/0288551 A1 | 9/2014 | Bharmi et al. |
| 2014/0288577 A1 | 9/2014 | Robinson et al. |
| 2014/0358024 A1 | 12/2014 | Nelson et al. |
| 2015/0018699 A1 | 1/2015 | Zeng et al. |
| 2015/0164354 A1 | 6/2015 | Parker et al. |
| 2015/0174396 A1 | 6/2015 | Fisher et al. |
| 2015/0238104 A1 | 8/2015 | Tass |
| 2015/0238304 A1 | 8/2015 | Lamraoui |
| 2015/0282725 A1 | 10/2015 | Single |
| 2015/0313487 A1 | 11/2015 | Single |
| 2015/0360031 A1 | 12/2015 | Bornzin et al. |
| 2015/0374999 A1 | 12/2015 | Parker |
| 2016/0166164 A1 | 6/2016 | Obradovic et al. |
| 2016/0287126 A1 | 10/2016 | Parker et al. |
| 2016/0287182 A1 | 10/2016 | Single |
| 2017/0001017 A9 | 1/2017 | Parker et al. |
| 2017/0049345 A1 | 2/2017 | Single |
| 2017/0071490 A1 | 3/2017 | Parker et al. |
| 2017/0135624 A1 | 5/2017 | Parker |
| 2017/0216587 A1 | 8/2017 | Parker |
| 2018/0110987 A1 | 4/2018 | Parker |
| 2018/0117335 A1 | 5/2018 | Parker et al. |
| 2018/0132747 A1 | 5/2018 | Parker et al. |
| 2018/0132760 A1 | 5/2018 | Parker |
| 2018/0133459 A1 | 5/2018 | Parker et al. |
| 2018/0228391 A1 | 8/2018 | Parker et al. |
| 2018/0228547 A1 | 8/2018 | Parker |
| 2018/0229046 A1 | 8/2018 | Parker et al. |
| 2018/0256052 A1 | 9/2018 | Parker et al. |
| 2019/0168000 A1 | 6/2019 | Laird-wah |
| 2019/0216343 A1 | 7/2019 | Single et al. |

FOREIGN PATENT DOCUMENTS

| | | |
|---|---|---|
| EP | 2019716 A | 11/2007 |
| EP | 2243510 A2 | 10/2010 |
| EP | 2443995 A2 | 4/2012 |
| EP | 2707095 A1 | 3/2014 |
| JP | 2012524629 | 10/2012 |
| JP | 2013527784 A | 7/2013 |
| JP | 2013536044 A | 9/2013 |
| WO | 1983003191 A | 9/1983 |
| WO | 1993001863 A1 | 2/1993 |
| WO | 9612383 A1 | 4/1996 |
| WO | 2000002623 A1 | 1/2000 |
| WO | 2002036003 A1 | 11/2001 |
| WO | 2002038031 | 5/2002 |
| WO | 2002049500 A2 | 6/2002 |
| WO | 2003028521 A2 | 4/2003 |
| WO | 2003043690 | 5/2003 |
| WO | 2003103484 | 12/2003 |
| WO | 2004021885 A1 | 3/2004 |
| WO | 20040103455 | 12/2004 |
| WO | 2005032656 A1 | 4/2005 |
| WO | 2005105202 A1 | 11/2005 |
| WO | 2006091636 A2 | 8/2006 |
| WO | 2007064936 A1 | 6/2007 |
| WO | 2007127926 A2 | 11/2007 |
| WO | 2007130170 A1 | 11/2007 |
| WO | 2008004204 A1 | 1/2008 |
| WO | 2008049199 A1 | 5/2008 |
| WO | 2009002072 A2 | 12/2008 |
| WO | 2009002579 A1 | 12/2008 |
| WO | 2009010870 A2 | 1/2009 |
| WO | 2009130515 A2 | 10/2009 |
| WO | 2009146427 A1 | 12/2009 |
| WO | 2010013170 A1 | 2/2010 |
| WO | 2010044989 A2 | 4/2010 |
| WO | 2010051392 A1 | 5/2010 |
| WO | 2010057046 A2 | 5/2010 |
| WO | 2010124139 A1 | 10/2010 |
| WO | 2010138915 A1 | 12/2010 |
| WO | 2011011327 A1 | 1/2011 |
| WO | 2011066477 A1 | 6/2011 |
| WO | 2011066478 A1 | 6/2011 |
| WO | 2011112843 A1 | 9/2011 |
| WO | 2011119251 A2 | 9/2011 |
| WO | 2011159545 A2 | 12/2011 |
| WO | 2012027252 A2 | 3/2012 |
| WO | 2012022791 A1 | 3/2012 |
| WO | 2012155183 A1 | 11/2012 |
| WO | 2012155184 A1 | 11/2012 |
| WO | 2012155185 A1 | 11/2012 |
| WO | 2012155187 A1 | 11/2012 |
| WO | 2012155188 A1 | 11/2012 |
| WO | 2012155189 A1 | 11/2012 |
| WO | 2012155190 A1 | 11/2012 |
| WO | 2013063111 A1 | 5/2013 |
| WO | 2013075171 A1 | 5/2013 |
| WO | 2014071445 A1 | 5/2014 |
| WO | 2014071446 A1 | 5/2014 |
| WO | 2014143577 A1 | 9/2014 |
| WO | 2015070281 A1 | 5/2015 |
| WO | 2015074121 A1 | 5/2015 |
| WO | 2015109239 A1 | 7/2015 |

(56) References Cited

FOREIGN PATENT DOCUMENTS

| WO | 2015143509 | A1 | 10/2015 |
|---|---|---|---|
| WO | 2015168735 | A1 | 11/2015 |
| WO | 20160011512 | | 1/2016 |
| WO | 2016077882 | A1 | 5/2016 |
| WO | 2016090420 | A1 | 6/2016 |
| WO | 2016090436 | A1 | 6/2016 |
| WO | 2016115596 | A1 | 7/2016 |
| WO | 2016161484 | A2 | 10/2016 |
| WO | 2016191807 | A1 | 12/2016 |
| WO | 2016191808 | A1 | 12/2016 |
| WO | 2016191815 | A1 | 12/2016 |
| WO | 2017173493 | A1 | 10/2017 |
| WO | 2017219096 | A1 | 12/2017 |

OTHER PUBLICATIONS

European Search Report for European Application 12785619.3, Search Completed Oct. 13, 2014, dated Oct. 23, 2014, 7 pgs.
Extended European Search Report for EP Application 12785483.4, completed Sep. 16, 2014, 7 pgs.
Kent et al., "Instrumentation to Record Evoked Potentials for Closed-Loop Control of Deep Brain Stimulation", Conf. Proc. IEEE Eng. Med Biol. Sol, Aug. 2012, 10 pgs.
International Search Report for International Application No. PCT/AU2012/000511, International Filing Date May 11, 2012, Search Completed May 17, 2012, dated May 18, 2012, 4 pgs.
International Search Report for International Application No. PCT/AU2012/000512, International Filing Date May 11, 2012, Search Completed Jul. 10, 2012, dated Jul. 11, 2012, 4 pgs.
International Search Report for International Application No. PCT/AU2012/000513, International Filing Date May 11, 2012, Search Completed May 29, 2012, dated May 30, 2012, 5 pgs.
International Search Report for International Application No. PCT/AU2012/000515, International Filing Date May 11, 2012, Search Completed May 21, 2012, dated Jun. 4, 2012, 5 pgs.
International Search Report for International Application No. PCT/AU2012/000516, International Filing Date May 11, 2012, Search Completed Jul. 11, 2012, dated Jul. 12, 2012, 8 pgs.
International Search Report for International Application No. PCT/AU2012/000517, International Filing Date May 11, 2012, Search Completed Jun. 4, 2012, dated Jun. 6, 2012, 3 pgs.
International Search Report for International Application No. PCT/AU2012/000518, International Filing Date May 11, 2012, Search Completed Jun. 8, 2012, dated Jun. 12, 2012, 4 pgs.
Written Opinion for International Application No. PCT/AU2012/000511, International Filing Date May 11, 2012, Search Completed May 17, 2012, dated May 18, 2012, 5 pgs.
Written Opinion for International Application No. PCT/AU2012/000512, International Filing Date May 11, 2012, Search Completed Jul. 10, 2012, dated Jul. 11, 2012, 7 pgs.
Written Opinion for International Application No. PCT/AU2012/000513, International Filing Date May 11, 2012, Search Completed May 29, 2012, dated May 30, 2012, 7 pgs.
Written Opinion for International Application No. PCT/AU2012/000515, International Filing Date May 11, 2012, Search Completed May 21, 2012, dated Jun. 4, 2012, 4 pgs.
Written Opinion for International Application No. PCT/AU2012/000516, International Filing Date May 11, 2012, Search Completed Jul. 11, 2012, dated Jul. 12, 2012, 8 pgs.
Written Opinion for International Application No. PCT/AU2012/000517, International Filing Date May 11, 2012, Search Completed Jun. 4, 2012, dated Jun. 6, 2012, 5 pgs.
Written Opinion for International Application No. PCT/AU2012/000518, International Filing Date May 11, 2012, Search Completed Jun. 8, 2012, dated Jun. 12, 2012, 10 pgs.
European Search Report for European Application 12785669.8, Search Completed Sep. 22, 2014, dated Sep. 29, 2014, 5 pgs.
International Search Report for Australian Application 2011901829, Search Completed Feb. 6, 2012, dated Feb. 7, 2012, 3pgs.

Andreassen, S. et al., "Muscle Fibre Conduction Velocity in Motor Units of the Human Anterior Tibial Muscle: a New Size Principle Parameter", J. Physiol. (1987), 391, pp. 561-571.
Blum, A. R., "An Electronic System for Extracellular Neural Stimulation and Recording", Dissertation, Georgia Institute of Technology, Aug. 2007, Retrieved from http://smartech.gatech.edu/handle/1853/16192 on Jan. 30, 2012.
Dawson, G. D., "The relative excitability and conduction velocity of sensory and motor nerve fibres in man", Journal of Physiology, 1956, vol. 131(2), pp. 436-451. Figs. 1-5; Table 1; p. 437 "Methods"; pp. 438-447 "Results".
Dijkstra, E. A., "Ultrasonic Distance Detection for a Closed-Loop Spinal Cord Stimulation System", Proceedings—19th International Conference—IEEE/EMBS Oct. 30-Nov. 2, 1997, Chicago, IL. p. 324 section 'Paraesthesia Coverage by Dermatome,' p. 326 section 'Total Paraesthesia Coverage' and Figures 1 and 6-10.
Dillier, N et al., "Measurement of the electrically evoked compound action potential via a neural response telemetry system", Ann. Otol. Rhinol. Laryngol. 111 (May 2002), No. 5, pp. 407-414. Abstract & Figures 2-3, 407-414.
Fagius, J. et al., "Sympathetic Reflex Latencies and Conduction Velocities in Normal Man", Journal of Neurological Sciences, 1980. vol. 47, pp. 433-448.
Goodall, E. V., "Modeling Study of Activation and Propagation delays During Stimulation of Peripheral Nerve Fibres with a Tripolar Cuff Electrode", IEEE Trans.Rehab.Eng. vol. 3, pp. 272-282.
Harper, A. A., "Conduction Velocity is Related to Morphological Cell Type in Rat Dorsal Root Ganglion Neurones", J. Physiol. (1985), 359, pp. 31-46.
Mahnam, A et al., "Measurement of the current-distance relationship using a novel refractory interaction technique", J. Neural Eng. 6 (2009), pp. 036005 (published May 20, 2009) Abstract, Sec. 2.2 & Figure 2b, 036005.
Massachusetts Institute of Techn, "The Compound Action Potential of the Frog Sciatic Nerve", Quantitative Physiology: Cells and Tissues. Fall, 1999, Retrieved from http://umech.mit.edu/freeman/6.021J/2001/lab.pdf on May 22, 2012.
McGill, Kevin et al., "On the Nature and Elimination of Stimulus Artifact in Nerve Signals Evoked and Recorded Using Surface Electrodes", IEEE Transactions on Biomedical Engineering, vol. BME-29, No. 2, Feb. 1982, pp. 129-137.
Opsommer, E. et al., "Determination of Nerve Conduction Velocity of C-fibres in Humans from Thermal Thresholds to Contact Heat (Thermode) and from Evoked Brain Potentials to Radiant Heat (CO2 Laser)", Neurophysiologie Clinique 1999, vol. 29, pp. 411-422.
Parker, J. L., "Compound Action Potentials Recorded in the Human Spinal Cord During Neurostimulation for Pain Relief", Pain, vol. 153, 2012, pp. 593-601.
Roy, S. H. et al., "Effects of Electrode Location on Myoelectric Conduction Velocity and Median Frequency Estimates", J. Appl. Physiol. 61 (4), 1986, pp. 1510-1517.
Tomas et al., "Dorsal Root Entry Zone (DREZ) Localization Using Direct Spinal Cord Stimulation Can Improve Results of the DREZ Thermocoagulation Procedure for Intractable Pain Relief", Pain, 2005, vol. 116, pp. 159-163.
Yearwood, T. L., "Pulse Width Programming in Spinal Cord Stimulation: a Clinical Study", Pain Physician. 2010. vol. 13, pp. 321-335.
Borg et al., "Conduction velocity and refractory period of single motor nerve fibres in antecedent poliomyelitis", Journal of Neurology, Neurosurgery, and Psychiatry, vol. 50, 1987, 443-446.
Orstavik, Kristin et al. "Pathological C-fibres in patients with a chronic painful condition", Brain (2003), 126, 567-578.
International Preliminary Report on Patentability for International Application No. PCT/AU2016/050263, Report dated Oct. 10, 2017, 9 pgs.
International Search Report and Written Opinion for International Application No. PCT/AU2016/050263, Search completed Nov. 16, 2016, dated Nov. 16, 2016, 8 Pgs.
International Search Report and Written Opinion for International Application No. PCT/AU2016/050430, Search completed Aug. 16, 2016, dated Aug. 16, 2016, 10 Pgs.

(56) References Cited

OTHER PUBLICATIONS

International Search Report and Written Opinion for International Application No. PCT/AU2016/050431, Search completed Aug. 16, 2016, dated Aug. 16, 2016, 11 Pgs.
International Search Report and Written Opinion for International Application No. PCT/AU2016/050439, Search completed Jul. 15, 2016, dated Jul. 15, 2016, 8 Pgs.
Alam et al., "Evaluation of optimal electrode configurations for epidural spinal cord stimulation in cervical spinal cord injured rats", Journal of Neuroscience Methods, Mar. 2015, 28 pgs.
Fisher, "F-Waves—Physiology and Clinical Uses", TheScientificWorldJournal, (2007) 7, pp. 144-160.
Gad et al., "Development of a multi-electrode array for spinal cord epidural stimulation to facilitate stepping and standing after a complete spinal cord injury in adult rats", Journal of NeuroEngineering and Rehabilitation 2013, 10:2, 18 pgs.
Sayenko et al., "Neuromodulation of evoked muscle potentials induced by epidural spinal-cord stimulation in paralyzed individuals", Journal of Neurophysiology, vol. 111, No. 5, 2014, pp. 1088-1099, First published Dec. 11, 2013.
Struijk et al., "Excitation of Dorsal Root Fibers in Spinal Cord Stimulation: a Theoretical Study", IEEE Transactions on Biomedical Engineering, Jul. 1993, vol. 40, No. 7, pp. 632-639.
Yamada et al., "Extraction and Analysis of the Single Motor Unit F-Wave of the Median Nerve", EMG Methods for Evaluating Muscle and Nerve Function, InTech, 2012, 15 pgs.
International Preliminary Report on Patentability for International Application No. PCT/AU2011/001127, Report dated Mar. 5, 2013, 9 pgs.
International Preliminary Report on Patentability for International Application No. PCT/AU2012/000511, Report dated Nov. 19, 2013, 6 pgs.
International Preliminary Report on Patentability for International Application No. PCT/AU2012/000512, Report dated Nov. 19, 2013, 8 pgs.
International Preliminary Report on Patentability for International Application No. PCT/AU2012/000513, Report dated Nov. 19, 2013, 11 pgs.
International Preliminary Report on Patentability for International Application No. PCT/AU2012/000515, Report dated Nov. 19, 2013, 5 pgs.
International Preliminary Report on Patentability for International Application No. PCT/AU2012/000516, Report dated Nov. 19, 2013, 9 pgs.
International Preliminary Report on Patentability for International Application No. PCT/AU2012/000517, Report dated Nov. 19, 2013, 6 pgs.
International Preliminary Report on Patentability for International Application No. PCT/AU2012/000518, Report dated Nov. 19, 2013, 11 pgs.
International Preliminary Report on Patentability for International Application No. PCT/AU2013/001279, Report dated May 12, 2015, 6 pgs.
International Preliminary Report on Patentability for International Application No. PCT/AU2013/001280, Report dated May 12, 2015, 6 pgs.
International Preliminary Report on Patentability for International Application No. PCT/AU2014/001049, Report dated May 17, 2016, 5 pgs.
International Preliminary Report on Patentability for International Application No. PCT/AU2014/050369, Report dated May 24, 2016, 8 pgs.
International Preliminary Report on Patentability for International Application No. PCT/AU2015/050135, Report dated Oct. 4, 2016, 13 pgs.
International Preliminary Report on Patentability for International Application No. PCT/AU2015/050215, Report dated Nov. 8, 2016, 4 pgs.
International Preliminary Report on Patentability for International Application No. PCT/AU2015/050422, Report dated Jan. 31, 2017, 8 pgs.
International Preliminary Report on Patentability for International Application No. PCT/AU2015/050787, Report dated Jun. 13, 2017, 6 pgs.
International Preliminary Report on Patentability for International Application No. PCT/AU2016/050019, Report dated Jul. 25, 2017, 9 pgs.
International Preliminary Report on Patentability for International Application No. PCT/AU2015/050724, Report dated May 23, 2017, 5 pgs.
International Preliminary Report on Patentability for International Application No. PCT/AU2015/050753, Report dated Jun. 13, 2017, 7 pgs.
Extended European Search Report for European Application No. 11820923.8, report completed Dec. 9, 2013, report dated Dec. 17, 2013, 6 pgs.
Extended European Search Report for European Application No. 13852669.4, Search completed Jun. 8, 2016, dated Jun. 22, 2016, 9 pgs.
Extended European Search Report for European Application No. 14861553.7, Search completed Jun. 8, 2017, dated Jun. 19, 2017, 8 pgs.
Extended European Search Report for European Application No. 14863597.2, Search completed Jun. 6, 2017, dated Jun. 13, 2017, 9 pgs.
Extended European Search Report for European Application no. 13853514.1, Search completed Jun. 8, 2016, dated Jun. 15, 2016, 07 pgs.
International Preliminary Report on Patentability for International Application No. PCT/AU2012/001441, Report dated May 27, 2014, 10 pgs.
International Search Report and Written Opinion for International Application No. PCT/AU2011/001127, date completed Nov. 11, 2011, dated Nov. 15, 2011, 13 pgs.
International Search Report and Written Opinion for International Application No. PCT/AU2012/001441, International Filing Date Nov. 23, 2012, Search Completed Feb. 26, 2013, dated Feb. 26, 2013, 14 pgs.
International Search Report and Written Opinion for International Application No. PCT/AU2014/001049, Search completed Feb. 10, 2015, dated Feb. 10, 2015, 8 pgs.
International Search Report and Written Opinion for International Application No. PCT/AU2014/050369, Search completed Feb. 20, 2015, dated Feb. 20, 2015, 14 pgs.
International Search Report and Written Opinion for International Application No. PCT/AU2015/050135, Search completed Jun. 30, 2015, dated Jun. 30, 2015, 26 pgs.
Miles et al., "An Electrode for Prolonged Stimulation of the Brain", Proc. 8th Meeting World Soc. Stereotactic and Functional Neurosurgery, Part III, Zurich, 1981, Appl. Neurophysiol, 45, 1982, pp. 449-445 1982.
Misawa et al., "Neuropathic Pain Is Associated with Increased Nodal Persistent Na(+) Currents in Human Diabetic Neuropathy", Journal of the Peripheral Nervous System: JPNS, 14, No. 4 (Dec. 2009): 279-284.
Nordin et al., "Ectopic Sensory Discharges and Paresthesiae in Patients with Disorders of Peripheral Nerves, Dorsal Roots and Dorsal Columns", Pain 20, No. 3 (Nov. 1984): 231-245, doi:10.1016/0304-3959(84)90013-7.
Oakley et al., "Spinal Cord Stimulation: Mechanisms of Action", Spine 27, No. 22, Nov. 15, 2002, pp. 2574-2583.
Oakley et al., "Transverse Tripolar Spinal Cord Stimulation: Results of an International Multicenter Study", Neuromodulation, vol. 9, No. 3, 2006, pp. 192-203.
Obradovic et al., "Effect of pressure on the spinal cord during spinal cord stimulation in an animal model", Poster, 18th Annual Meeting of the North American Neuromodulation Society, Dec. 11-14, 2014, Las Vegas.
Oh et al., "Long-term hardware-related complications of deep brain stimulation", Neurosurgery, vol. 50, No. 6, Jun. 2002, pp. 1268-1274, discussion pp. 1274-1276.

(56) References Cited

OTHER PUBLICATIONS

Parker et al., "Closing the Loop in Neuromodulation Therapies: Spinal Cord Evoked Compound Action Potentials During Stimulation for Pain Management (230)", 2011, In 15th Annual Meeting, North American Neuromodulation Society (p. 48). Presented at the North American Neuromodulation Society, Las Vegas.
Parker et al., "Compound action potentials recorded in the human spinal cord during neurostimulation for pain relief", Pain, 2012, vol. 153, pp. 593-601.
Parker et al., "Electrically Evoked Compound Action Potentials Recorded From the Sheep Spinal Cord", Neuromodulation, vol. 16, 2013, pp. 295-303.
Penar et al., "Cortical Evoked Potentials Used for Placement of a Laminotomy Lead Array: A Case Report", Neuromodulation: Technology at the Neural Interface, accessed Apr. 19, 2011, doi:10.1111/j.1525-1403.2011.00352.x.
Richter et al., "EMG and SSEP Monitoring During Cervical Spinal Cord Stimulation", Journal of Neurosurgical Review 2011, Southern Academic Press, 1(S1), 2011, pp. 61-63.
Ridder et al., "Burst Spinal Cord Stimulation for Limb and Back Pain", World Neurosurgery, 2013, 9 pgs.
Ridder et al., "Burst Spinal Cord Stimulation toward Paresthesia-Free Pain Suppression", May 2010, vol. 66, pp. 986-990.
Schmidt et al., "Gating of tactile input from the hand", Exp Brain Res, 1990, 79, pp. 97-102.
Siegfried et al., "Bilateral Chronic Electrostimulation of Ventroposterolateral Pallidum: A New Therapeutic Approach for Alleviating all Parkinsonian Symptoms", Neurosurgery, 35, No. 6, Dec. 1994, pp. 1126-1130.
Siegfried et al., "Intracerebral Electrode Implantation System", Journal of Neurosurgery, vol. 59, No. 2, Aug. 1983, pp. 356-3591.
Srinivasan, S, "Electrode/Electrolyte Interfaces: Structure and Kinetics of Charge Transfer", Fuel Cells, 2006, Chapter 2, 67 Pages.
Struijk et al, "Paresthesia Thresholds in Spinal Cord Stimulation: A Comparison of Theoretical Results with Clinical Data", IEEE Transactions on Rehabilitation Engineering, vol. 1, No. 2, Jun. 1993, pp. 101-108.
Sufka et al., "Gate Control Theory Reconsidered", Brain and Mind, 3, No. 2, 2002, pp. 277-290.
Tamura et al., "Increased Nodal Persistent Na+ Currents in Human Neuropathy and Motor Neuron Disease Estimated by Latent Addition", Clinical Neurophysiology 117, No. 11 (Nov. 2006): 2451-2458, doi:10.1016/j.clinph.2006.07.309.
Tasker, "Deep Brain Stimulation is Preferable to Thalamotomy for Tremor Suppression", Surgical Neurology, 49, No. 2, 1998, pp. 145-153.
Taylor et al., "Spinal Cord Stimulation for Chronic Back and Leg Pain and Failed Back Surgery Syndrome: A Systematic Review and Analysis of Prognostic Factors", SPINE, vol. 30, No. 1, 2004, pp. 152-160.
Texas Instruments, "Precision, Low Power Instrumentation Amplifiers", Texas Instruments SBOS051B Oct. 1995, Revised Feb. 2005, 20 pgs.
Tscherter et al., "Spatiotemporal Characterization of Rhythmic Activity in Rat Spinal Cord Slice Cultures", European Journal of Neuroscience 14, No. 2 (2001), pp. 179-190.
Van Den Berg et al., "Nerve fiber size-related block of action currents by phenytoin in mammalian nerve", Epilepsia, Nov. 1994, 35(6), pp. 1279-1288.
Villavicencio, Alan T. "Laminectomy versus Percutaneous Electrode Placement for Spinal Cord Stimulation," Neurosurgery, vol. 46 (2), Feb. 2000, pp. 399-405.
Vleggeert et al., LANKAMP "Electrophysiology and morphometry of the Aalpha- and Abeta-fiber populations in the normal and regenerating rat sciatic nerve", Experimental Neurology, vol. 187, No. 2, Jun. 1, 2004, Available online Apr. 2, 2004, pp. 337-349.
Woessner, "Blocking Out the Pain, Electric Nerve Block Treatments for Sciatic Neuritis", Retrieved from: http://www.practicalpainmanagement.com/pain/spine/radiculopathy/blocking-out-pain, Last updated Jan. 10, 2012.

Wolter et al., "Effects of sub-perception threshold spinal cord stimulation in neuropathic pain: A randomized controlled double-blind crossover study", European Federation of International Association for the Study of Pain Chapters, 2012, pp. 648-655.
Wu et al., "Changes in Aβ Non-nociceptive Primary Sensory Neurons in a Rat Model of Osteoarthritis Pain", Molecular Pain 6, No. 1 (Jul. 1, 2010): 37, doi: 10.1186/1744-8069-6-37.
Xie et al., "Functional Changes in Dorsal Root Ganglion Cells after Chronic Nerve Constriction in the Rat", Journal of Neurophysiology 73, No. 5 (May 1, 1995): 1811-1820.
Xie et al., "Sinusoidal Time-Frequency Wavelet Family and its Application in Electrograstrographic Signal Analysis", Proceedings of the 20th Annual International Conference of the IEEE Engineering in Medicine and Biology Society, vol. 20, No. 3, Oct. 29, 1998, pp. 1450-1453.
Yingling et al., "Use of Antidromic Evoked Potentials in Placement of Dorsal Cord Disc Electrodes", Applied Neurophysiology, 1986, vol. 49, pp. 36-41.
Extended European Search Report for European Application No. 15768956.3, Search completed Oct. 3, 2017, dated Oct. 10, 2017, 8 Pgs.
International Type Search Report for International Application No. AU2015902393, Search completed May 16, 2016, dated May 16, 2016, 8 Pgs.
International Search Report and Written Opinion for International Application No. PCT/AU2015/050422, Search completed Oct. 14, 2015, dated Oct. 14, 2015, 17 pgs.
International Search Report and Written Opinion for International Application No. PCT/AU2015/050724, Search completed May 9, 2016, dated May 9, 2016, 8 pgs.
International Search Report and Written Opinion for International Application No. PCT/AU2015/050753, Search completed Feb. 10, 2016, dated Feb. 10, 2016, 10 pgs.
International Search Report and Written Opinion for International Application No. PCT/AU2015/050787, Search completed Mar. 16, 2016, dated Mar. 16, 2016, 10 pgs.
International Search Report and Written Opinion for International Application No. PCT/AU2016/050019, Search completed May 4, 2016, dated May 4, 2016, 16 pgs.
International Search Report and Written Opinion for International Application No. PCT/AU2015/050215, Search completed Jul. 30, 2015, dated Jul. 30, 2015, 8 pgs.
Medtronic, Spinal Cord Stimulation, RestoreSensor Neurostimulator, Features and Specification: Specification, Printed Jun. 16, 2014, 2 pgs.
Medtronic, Spinal Cord Stimulation, RestoreSensor Neurostimulator, Features and Specification: Summary Printed Jun. 16, 2014, 1 pg.
Medtronic, RestoreSensor Neurostimulator, Retrieved from: http://web.archive.org/web/20150328092923/http://professional.medtronic.com:80/pt/neuro/scs/prod/restore-sensor/features-specifications/index.htm, Capture Date Jul. 9, 2012, Printed on May 11, 2017.
"Advanced Pain Therapy using Neurostimulation for Chronic Pain", Medtronic RestoreSensor clinical trial paper,Clinical summary, Nov. 2011, pp. 32.
"Battelle Neurotechnology—Moving Beyond the Limits in Neurotechnology", Battelle, www.battelle.org, May 2014, pp. 1-2.
"Haptic technology", Wikipedia, Retrieved from: http://en.wikipedia.org/wiki/Haptic_technology, Last modified on Sep. 15, 2014, Printed on Sep. 15, 2014, 5 pgs.
"Implants for surgery, Cardiac pacemakers", IS-1 standard ISO 5841-3-2000, Oct. 15, 2000.
"International Search Report", International Search Report & Written Opinion for International Application No. PCT/AU2013/001280, Search Completed Jan. 16, 2014, dated Jan. 16, 2014, 8 pgs.
"International Search Report", International Search Report & Written Opinion for International Application PCT/AU2013/001279, Search Completed Jan. 9, 2014, dated Jan. 9, 2014, 9 pgs.
"Neural Bypass Technology Enables Movement in Paralyzed Patient", Posted on Jul. 29, 2014, 6 a.m. in Brain chips/computer interface, pp. 1-2.

(56) References Cited

OTHER PUBLICATIONS

"Spinal Cord Stimulation, About Spinal Cord Stimulation", Medtronic, Retrieved from: http://professional.medtronic.com/pt/neuro/scs/edu/about/index.htm, Printed on Jun. 16, 2014, 2 pgs.

"Wide bandwidth BioAmplifier", http://www.psylab.com/html/default_bioamp.htm, Printed Jan. 30, 2014, 1-3 pages.

Andy, "Parafascicular-Center Median Nuclei Stimulation for Intractable Pain and Dyskinesia (Painful-Dyskinesia)", Stereotactic and Functional Neurosurgery, Appl. Neurophysiol., 43, No. 3-5, 1980, pp. 133-144.

Balzer et al., "Localization of cervical and cervicomedullary stimulation leads for pain treatment using median nerve somatosensay evoked potential collision testing", Journal of Neurosurgery, Jan. 2011, vol. 114, No. 1: pp. 200-205.

Brown et al., "Impact of Deep Brain Stimulation on Upper Limb Askinesia in Parkinson's Disease", Annals of Neurology, 45, No. 4, 1999, pp. 473-488.

Budagavi et al., "Modelling of compound nerve action potentials health and disease", Engineering in Medicine and Biology Society, 1992 14th Annual International Conference of the IEEE. vol. 6. IEEE, 1992, pp. 2600-2601.

Coquery et al., "Backward and forward masking in the perception of cutaneous stimuli", Perception & Psychophysics, 1973, vol. 13.No. 2, pp. 161-163.

Devergnas et al., A "Cortical potentials evoked by deep brain stimulation in the subthalamic area", Front Syst Neurosci. 2011; 5: 30. May 13, 2011. doi:10.3389/fnsys.2011.00030.

Doiron et al., "Persistent Na+ Current Modifies Burst Discharge by Regulating Conditional Backpropagation of Dendritic Spikes", Journal of Neurophysiology 89, No. 1 (Jan. 1, 2003): 324-337, doi:10.1152/jn.00729.2002.

England et al., "Increased Numbers of Sodium Channels Form Along Demyelinated Axons", Brain Research 548, No. 1-2 (May 10, 1991): 334-337.

Falowski et al., "Spinal Cord Stimulation: an update", Neurotherapeutics: The Journal of the American Society for Experimental NeuroTherapeutics 5, No. 1, Jan. 2008, pp. 86-99.

Franke et al., FELIX "An Online Spike Detection and Spike Classification Algorithm Capable of Instantaneous Resolution of Overlapping Spikes", Journal of Computational Neuroscience, 2010, vol. 29, No. 1-2, pp. 127-148.

Fuentes et al., "Spinal Cord Stimulation Restores Locomotion in Animal Models of Parkinson's Disease", Science, vol. 323, No. 5921, Mar. 20, 2009, pp. 1578-1582.

George et al., "Vagus nerve stimulation: a new tool for brain research and therapy", Biological Psychiatry 47, No. 4, Feb. 15, 2000, pp. 287-295.

Gorman et al., "ECAP Mapping of the Spinal Cord: Influence of Electrode Position on Aβ Recruitment", (2012). In 16th Annual Meeting. Presented at the North American Neuromodulation Society, Las Vegas, NV.

Gorman et al., "Neural Recordings for Feedback Control of Spinal Cord Stimulation: Reduction of Paresthesia Variability", 2013, In International Neuromodulation Society 11th World Congress. Presented at the International Neuromodulation Society 11th World Congress, Berlin, Germany.

Hallstrom et al, "Distribution of lumbar spinal evoked potentials and their correlation with stimulation-induced paresthesiae", (1991), Electroencephalography and clinical neurophysiology 80:126-139.

Holsheimer et al., "Optimum Electrode Geometry for Spinal Cord Stimulation: the Narrow Bipole and Tripole", Medical and Biological Engineering and Computing, 35, No. 5, 1997, pp. 493-497.

Huff, Terry B. et al., "Real-Time CARS Imaging Reveals a Calpain-Dependent Pathway for Paranodal Myelin Retraction during High-Frequency Stimulation", PLoS ONE vol. 6, issue 3 (Mar. 3, 2011): e17176, 11 pgs.

Hui, Ouyang, et al., "Compression Induces Acute Demyelination and Potassium Channel Exposure in Spinal Cord", Journal of Neurotrauma 27, No. 6, Jun. 2010, 1109-1120, doi:10.1089/neu.2010.1271.

Kent et al., AR "Recording evoked potentials during deep brain stimulation: development and validation of instrumentation to suppress the stimulus artefact", J Neural Eng. Jun. 2012; 9 (3):036004, Apr. 18, 2012. doi: 10.1088/1741-2560/9/3/036004.

Kim et al., "A Wavelet-Based Method for Action Potential Detection From Extracellular Neural Signal Recording With Low Signal-to-Noise Ratio", IEEE Transactions on Biomedical Engineering, vol. 50. No. 8, Aug. 2003.

Kim et al., "Cell Type-specific Changes of the Membrane Properties of Peripherally-axotomized Dorsal Root Ganglion Neurons in a Rat Model of Neuropathic Pain", Neuroscience 86, No. 1 (May 21, 1998): 301-309, doi:10.1016/S0306-4522(98)00022-0.

Krames et al., "Neuromodulation", 1st Edition, Academic Press, 2009, p. 540-541.

Krarup, Christian, "Compound sensory action potential in normal and pathological human nerves", Muscle & nerve, vol. 29, No. 4 (2004), pp. 465-483.

Krishnan et al., "Excitability Differences in Lower-Limb Motor Axons During and After Ischemia", Muscle & nerve, vol. 31, No. 2 (2005), pp. 205-213.

Kumar et al., "Deep Brain Stimulation for Intractable Pain: a 15-year Experience", Neurosurgery, Issue 40, No. 4, Apr. 1997, pp. 736-747.

Kumar et al., "Double-blind evaluation of subthalamic nucleus deep brain stimulation in advanced Parkinson's disease", by the American Academy of Neurology, 51, No. 3, Sep. 1, 1998, pp. 850-855.

Kumar et al., "Globus Pallidus Deep Brain Stimulation for Generalized Dystonia: Clinical and PET Investigation", Neurology, 53, No. 4, 1999, pp. 871-874.

Laird et al., "A Model of Evoked Potentials in Spinal Cord Stimulation", IEEE Engineering in Medicine & Biology Society, 35th Annual Conference. Osaka, Japan: Jul. 3-7, 2013, pp. 6555-6558.

Lempka, Scott, "The Electrode-Tissue Interface During Recording and Stimulation in the Central Nervous System", published on May 2010.

Levy et al., "Incidence and Avoidance of Neurologic Complications with Paddle Type Spinal Cord Stimulation Leads", Neuromodulation 14(15), Sep. 2011, pp. 412-422.

Li et al., S, "Resonant antidromic cortical circuit activation as a consequence of high-frequency subthalamic deep-brain stimulation", J Neurophysiol. Dec. 2007; 98(6): 3525-37. First published Oct. 10, 2007. doi:10.1152/jn.00808.2007.

Ma et al., "Similar Electrophysiological Changes in Axotomized and Neighboring Intact Dorsal Root Ganglion Neurons", Journal of Neurophysiology 89, No. 3 (Mar. 1, 2003): 1588-1602, doi:10.1152/jn.00855.2002.

Macefield, "Spontaneous and Evoked Ectopic Discharges Recorded from Single Human Axons", Muscle & Nerve 21, No. 4, Apr. 1998, pp. 461-468.

Markandey, Vishal, "ECG Implementation on the TMS320C5515 DSP Medical Development Kit (MDK)", Texas Instruments Application Report Jun. 2010, 35 pgs.

Matzner et al., "Na+ Conductance and the Threshold for Repetitive Neuronal Firing", Brain Research 597, No. 1 (Nov. 27, 1992): 92-98, doi:10.1016/0006-8993(92)91509-D.

Melzack et al., "Pain mechanisms: a new theory", Science, New York, New York, vol. 150, No. 3699, Nov. 19, 1965, pp. 971-979.

Extended European Search Report for European Application No. 16739680.3, Search completed Jun. 1, 2018, dated Jun. 12, 2018, 9 Pgs.

Al-Ani et al., "Automatic removal of high-amplitude stimulus artefact from neuronal signal recorded in the subthalamic nucleus", Journal of Neuroscience Methods, vol. 198, Issue 1, 2011, pp. 135-146.

French et al., "Information transmission at 500 bits/s by action potentials in a mechanosensory neuron of the cockroach", Neuroscience Letters, vol. 243, No. 1-3, Feb. 1, 1998, pp. 113-116.

Herreras, "Local Field Potentials: Myths and Misunderstandings", Frontiers in Neural Circuits, Dec. 15, 2016, 16 pgs.

European Search Report for European Application No. 15861444.6, Search completed Jul. 13, 2018, dated Jul. 23, 2018, 8 pgs.

(56) References Cited

OTHER PUBLICATIONS

International Search Report and Written Opinion for International Application No. PCT/AU2017/050296, Search completed Jul. 28, 2017, dated Jul. 28, 2017, 10 pgs.
He et al., "Perception threshold and electrode position for spinal cord stimulation", Pain, 59 (1994) 55-63 pages.
Holsheimer et al., "Significance of the Spinal Cord Position in Spinal Cord Stimulation", Acta Neurochir (1995) [Suppl] 64: 119-124 pages.
Holsheimer et al., "Spinal Geometry and Paresthesia Coverage in Spinal Cord Stimulation", (1998 paper) 8 pages.
Olin et al., "Postural Changes in Spinal Cord Stimulation Perceptual Thresholds", Neuromodulation, vol. 1, No. 4, 1998, pp. 171-175.
Rattay, "Analysis of Models for External Stimulation of Axons", IEEE Transactions on Biomedical Engineering, vol. BME-33, No. 10, Oct. 1986, pp. 974-977.
Ross et al., "Improving Patient Experience with Spinal Cord Stimulation: Implications of Position-Related Changes in Neurostimulation", Neuromodulation 2011; e-pub ahead of print. DOI: 10.1111/j.1525-1403.2011.00407.x 6 pages.
Struijk, "The Extracellular Potential of a Myelinated Nerve Fiber in an Unbounded Medium and in Nerve Cuff Models", Biophysical Journal, vol. 72, Jun. 1997, pp. 2457-2469.
Extended European Search Report for European Application No. 16802237.4, Search completed Dec. 11, 2018, dated Dec. 19, 2018, 9 Pgs.
Extended European Search Report for European Application No. 16802238.2, Search completed Oct. 17, 2018, dated Oct. 24, 2018, 8 Pgs.
International Preliminary Report for International Application No. PCT/AU2017/050296, dated Oct. 9, 2018, 7 Pgs.
International Preliminary Report for International Application No. PCT/AU2017/050647, dated Dec. 25, 2018, 8 pgs.
International Search Report and Written Opinion for International Application No. PCT/AU2017/050647, Search completed Sep. 29, 2017, dated Sep. 29, 2017, 13 Pgs.
Partial European Search Report for European Application No. 16775966.1, Search completed Oct. 26, 2018, dated Nov. 6, 2018, 11 Pgs.
Bahmer et al., "Application of triphasic pulses with adjustable phase amplitude ratio (PAR) for cochlear ECAP recording: I. Amplitude growth functions", Journal of Neuroscience Methods, Clinical Neuroscience, 2012, vol. 205, pp. 202-211.
Bahmer et al., "Effects of electrical pulse polarity shape on intra cochlear neural responses in humans: Triphasic pulses with cathodic second phase", Hearing Research, 2013, vol. 306, pp. 123-130.
Gnadt et al., "Spectral Cancellation of Microstimulation Artifact for Simultaneous Neural Recording In Situ", IEEE Transactions on Biomedical Engineering, Oct. 2003, Date of Publication: Sep. 23, 2003, vol. 50, No. 10, pp. 1129-1135, DOI: 10.1109/TBME.2003.816077.
Jeffrey et al., "A reliable method for intracranial electrode implantation and chronic electrical stimulation in the mouse brain", BMC Neuroscience. Biomed Central. London. GB. vol. 14, No. 1, Aug. 6, 2013, p. 82.
Tronnier et al., "Magnetic Resonance Imaging with Implanted Neurostimulators: An In Vitro and In Vivo Study", Jan. 1999, Neurosurgery, vol. 44(1), p. 118-125.

\* cited by examiner

METHOD AND APPARATUS FOR MEASUREMENT OF NEURAL RESPONSE

CROSS-REFERENCE TO RELATED APPLICATIONS

This application is a national stage of Application No. PCT/AU2012/000513, filed May 11, 2012, which application claims the benefit of Australian Provisional Patent Application No. 2011901826 filed May 13, 2011 and Australian Provisional Patent Application No. 2011901817 filed May 13, 2011, the disclosures of which are incorporated herein by reference in their entireties.

TECHNICAL FIELD

The present invention relates to measurement of a neural response to a stimulus, and in particular relates to measurement of a compound action potential by using one or more electrodes implanted proximal to the neural pathway.

BACKGROUND OF THE INVENTION

There are a range of situations in which it is desirable to measure a compound action potential (CAP). For example, neuromodulation is used to treat a variety of disorders including chronic pain, Parkinson's disease, and migraine. A neuromodulation system applies an electrical pulse to tissue in order to generate a therapeutic effect. When used to relieve chronic pain, the electrical pulse is applied to the dorsal column (DC) of the spinal cord. Such a system typically comprises an implanted electrical pulse generator, and a power source such as a battery that may be rechargeable by transcutaneous inductive transfer. An electrode array is connected to the pulse generator, and is positioned in the dorsal epidural space above the dorsal column. An electrical pulse applied to the dorsal column by an electrode causes the depolarisation of neurons, and generation of propagating action potentials. The fibres being stimulated in this way inhibit the transmission of pain from that segment in the spinal cord to the brain. To sustain the pain relief effects, stimuli are applied substantially continuously, for example at 100 Hz.

While the clinical effect of spinal cord stimulation (SCS) is well established, the precise mechanisms involved are poorly understood. The DC is the target of the electrical stimulation, as it contains the afferent Aβ fibres of interest. Aβ fibres mediate sensations of touch, vibration and pressure from the skin. The prevailing view is that SCS stimulates only a small number of Aβ fibres in the DC. The pain relief mechanisms of SCS are thought to include evoked antidromic activity of Aβ fibres having an inhibitory effect, and evoked orthodromic activity of Aβ fibres playing a role in pain suppression. It is also thought that SCS recruits Aβ nerve fibres primarily in the DC, with antidromic propagation of the evoked response from the DC into the dorsal horn thought to synapse to wide dynamic range neurons in an inhibitory manner.

Neuromodulation may also be used to stimulate efferent fibres, for example to induce motor functions. In general, the electrical stimulus generated in a neuromodulation system triggers a neural action potential which then has either an inhibitory or excitatory effect. Inhibitory effects can be used to modulate an undesired process such as the transmission of pain, or to cause a desired effect such as the contraction of a muscle.

The action potentials generated among a large number of fibres sum to form a compound action potential (CAP). The CAP is the sum of responses from a large number of single fibre action potentials. The CAP recorded is the result of a large number of different fibres depolarising. The propagation velocity is determined largely by the fibre diameter and for large myelinated fibres as found in the dorsal root entry zone (DREZ) and nearby dorsal column the velocity can be over 60 ms$^{-1}$. The CAP generated from the firing of a group of similar fibres is measured as a positive peak potential P1, then a negative peak N1, followed by a second positive peak P2. This is caused by the region of activation passing the recording electrode as the action potentials propagate along the individual fibres.

To better understand the effects of neuromodulation and/or other neural stimuli, it is desirable to record a CAP resulting from the stimulus. However, this can be a difficult task as an observed CAP signal will typically have a maximum amplitude in the range of microvolts, whereas a stimulus applied to evoke the CAP is typically several volts. To resolve a 10 µV spinal cord potential (SCP) with 1 µV resolution in the presence of an input 5V stimulus, for example, requires an amplifier with a dynamic range of 134 dB, which is impractical in implant systems. CAP recordings are sometimes made during surgical procedures on the spinal cord, to provide an indication of any potential neurological damage being caused by the procedure. Typically, a site below (caudally of) the area being operated on is stimulated and recordings are made above (rostrally of) the site. A diminishing response, or a change in response, is taken to indicate a change in the neurological condition of the spinal cord and may indicate that lasting damage has been caused by the procedure. For example such monitoring is often performed during scoliosis surgery (straightening a curvature of the spine) to ensure that the decompression doesn't damage the spinal cord. Somatosensory potentials are also used for spinal cord monitoring during surgery. These are recorded on the scalp of the patient and are evoked from stimulation of a peripheral nerve, usually one of the tibial nerve, median nerve or ulnar nerve. Somatosensory potentials can also be measured in response to stimulation of the spinal cord. For dorsal root entry zone (DREZ) lesioning surgery, it has been proposed to take point measurements of evoked potentials in order to identify a suitable site for the DREZ lesioning to occur.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

SUMMARY OF THE INVENTION

According to a first aspect the present invention provides a method for determining a desired location at which to apply a neural therapy, the method comprising:

positioning an array of electrodes proximal to neural tissue;

applying a stimulus from the array which evokes a neural compound action potential response in the neural tissue proximal to the array;

using a plurality of electrodes of the array to simultaneously obtain respective measurements of the neural compound action potential response; and determining from the measurements of the neural compound action potential response a desired location for a neural therapy.

According to a second aspect the present invention provides a system for determining a desired location at which to apply a neural therapy, the system comprising:

an array of electrodes configured to be positioned proximal to neural tissue;

a control unit configured to cause application of a stimulus from the array which evokes a neural compound action potential response in the neural tissue proximal to the array, the control unit further configured to simultaneously obtain a plurality of measurements of the neural compound action potential response from a plurality of electrodes of the array, and the control unit further configured to determine from the measurements of the neural compound action potential response a desired location for a neural therapy.

The present invention thus provides for selecting a neural therapy location by contemporaneously measuring local neural activity at a number of sites alongside the array. Simultaneously obtaining measurements of the neural response at a plurality of locations avoids variations which may arise when measuring responses to different stimuli, and which may introduce error in comparisons between sequentially obtained measurements. Moreover, simultaneous measurements are more rapid than sequentially obtained measurements of the neural response, particularly if electrode relocation is required between sequential stimuli.

The array preferably comprises a large number of electrodes configured to obtain simultaneous measurements of a neural compound action potential response, in order to yield fine spatial resolution of the neural sensitivity map of the area alongside the array. For example the array may comprise 24 electrodes arranged in 3 columns and 8 rows, or more.

In some embodiments, the method of the present invention may be applied intra-operatively in order to provide intra-operative information regarding the neural compound action potential response. In some embodiments of the invention, the method may be used for intra-operative DREZ localization, by generating a neural sensitivity map around the DREZ in order to guide DREZ lesioning. In such embodiments, the DREZ lesioning may be performed in progressive increments, iteratively with neural sensitivity mapping, whereby the ongoing neural sensitivity mapping provides a progressive intra-operative gauge of the effects of lesioning. In some embodiments of the invention, the DREZ lesioning may be performed by RF ablation, applied from the same electrode array as is used for the sensitivity mapping. Such embodiments provide for the same device to be used for sensitivity mapping and for lesioning, thereby eliminating the need to remove the measuring tools to allow lesioning to occur and eliminating errors which may arise in location determination during intra-operative re-positioning of the measurement and lesioning devices. Other applications of the invention could include surgical monitoring such as scoliosis surgery, spinal cord tumour, spinal cord hypothermia during aortic surgery, spinal cord ischemia during aortic surgery, TCE-evoked electromyograms during thoracoabdominal aortic surgery, or diagnoses such as spinal cord potentials in patients with ALS, spinal cord potentials in patients with tabes dorsalis, and spinal cord potentials in patients with spinal tumours.

Still further embodiments of the invention may use the method intra-operatively in order to optimize the position of an electrode or electrode array being implanted. In such embodiments the neural response measurements may be obtained from the same array as is being implanted, or alternatively may be obtained from a separate array, with stimuli being applied by the electrode(s) undergoing implantation. For example, such embodiments may be used for intra-operative positioning of an electrode array being implanted, laterally relative to the spinal cord, for example in order to align the array with the dorsal horn. Such embodiments recognise that variations occur in the evoked response amplitude relative to a lateral distance from the dorsal horn. Intra-operative information may be presented to a surgeon by way of a simple amplitude meter, an audible signal undergoing pitch or volume variations, or otherwise. Embodiments used for intra-operative electrode positioning may also include caudorostral positioning of an electrode or array being implanted, as neural sensitivity mapping will be influenced by inter-segment fibre density variations thereby permitting caudorostral positioning. The ECAP magnitude and stimulus threshold can vary by a factor of two with varying lateral and caudorostral position. The choice of stimulating electrode can therefore have a profound effect on the power consumption for an implanted stimulator for SCS. Embodiments used for intra-operative electrode positioning may also include intra-operative positioning of a peripheral nerve stimulator, for example an occipital nerve stimulator.

Additionally or alternatively, in some embodiments the measurements of the neural response may be obtained occasionally or on an ongoing basis post-operatively, for example in order to give ongoing guidance as to the suitability of the site of the neural therapy. Such embodiments may further provide for manual or automated re-fitting of a therapeutic device whereby a site of the neural therapy is revised in response to the ongoing measurements. For example, where an electrode array is used to apply the neural therapy, a selection of which electrode(s) to use to apply a therapeutic stimulus may be altered in response to the ongoing measurements and an updated map of spinal cord sensitivity as measured at each electrode.

Further embodiments of the invention may provide for post-operatively mapping spinal cord sensitivity to peripheral stimuli, to refine the selection of which electrode (location) in an array to use to apply spinal stimuli. For example, the spinal neural sensitivity map may change over time in response to changed pathology, or may change in response to relative movement between implant and spinal cord whether caused by device migration or by postural changes.

In some embodiments of the invention, the stimulus is applied repeatedly and the evoked spinal responses are measured repeatedly, with the measurements being averaged over a number of such cycles to improve SNR and improve the neural sensitivity map produced.

In further embodiments of the invention, the stimulus may be applied under the control of a remote control of the implanted array. For example, a peripheral stimulus such as a TENS stimulus may be applied by holding the remote control unit against the desired stimulus site.

The stimulus may be a physical stimulus for example manipulation of an extremity of a person. Additionally or alternatively, the stimulus may be applied by a transcutaneous electrical nerve stimulator (TENS) at the periphery.

Additionally or alternatively, the stimulus may be an electrical neural stimulus applied directly to a neural pathway. The stimulus may be applied by the same electrode array as is used to measure the neural response.

According to another aspect the present invention provides a computer program product comprising computer program code means to make a computer execute a procedure for determining a desired location at which to apply a neural therapy, the computer program product comprising computer program code means for carrying out the method of the first aspect.

BRIEF DESCRIPTION OF THE DRAWINGS

An example of the invention will now be described with reference to the accompanying drawings, in which.

An example of the invention will now be described with reference to the accompanying drawings, in which.

DESCRIPTION OF THE PREFERRED EMBODIMENTS

Figure 1:
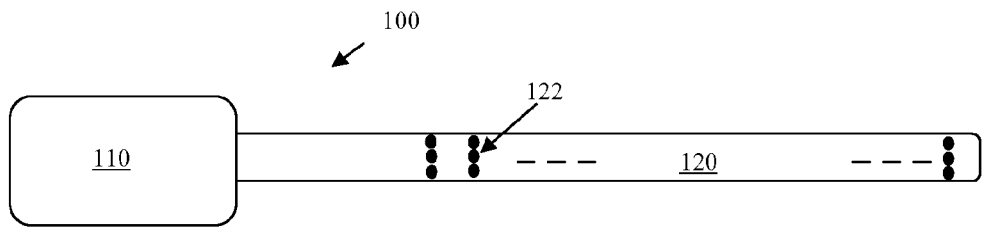
FIG. 1 illustrates an implantable device suitable for implementing the present invention.

FIG. 1 illustrates an implantable device 100 suitable for implementing the present invention. Device 100 comprises an implanted control unit 110, which controls application of neural stimuli, and controls a measurement process for obtaining a measurement of a neural response evoked by the stimuli from each of a plurality of electrodes. Device 100 further comprises an electrode array 120 consisting of a three by eight array of electrodes 122, each of which may be selectively used as either the stimulus electrode or sense electrode, or both.

Figure 2:
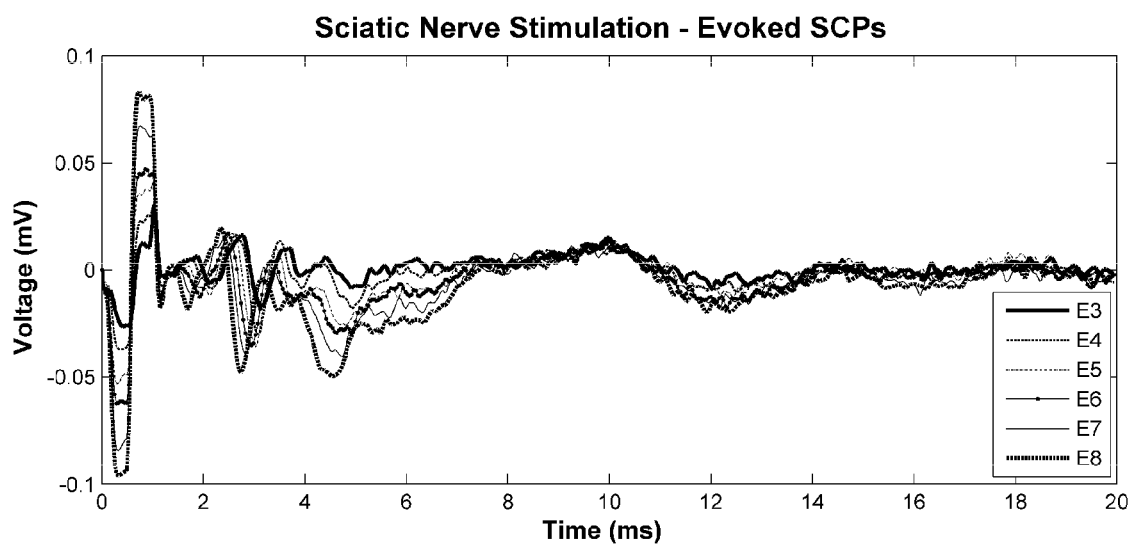
FIG. 2 illustrates a plurality of simultaneously recorded measurements of a neural response in an ovine spinal cord as a result of stimulation of the sciatic nerve.
Figure 2:
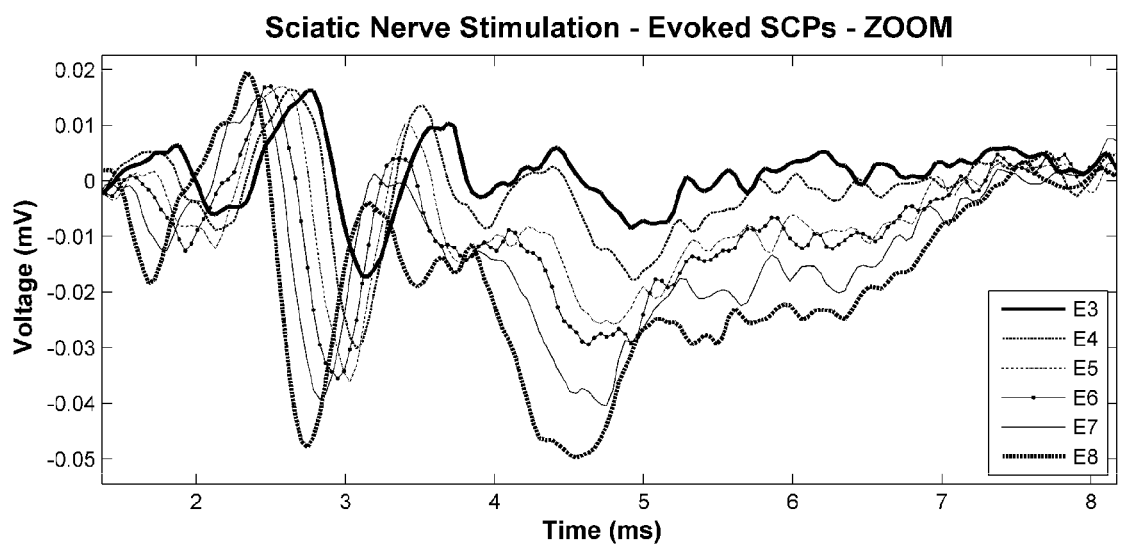

FIG. 2 illustrates a neural compound action potential response in an ovine spinal cord resulting from electrical stimulation of the sciatic nerve, as recorded simultaneously on 6 electrodes. In FIG. 2, the upper trace shows 20 ms of each recording, while the lower trace shows about 8 ms of the same recordings, all made simultaneously of a single neural response. As can be seen in FIG. 2, the time of arrival of the neural response is slightly different at each sense electrode, reflecting the time taken for the neural response to travel between electrodes in the array 120. As can also be seen in FIG. 2, the peak-to-peak amplitude of each measurement differs somewhat, particularly noticeable in the fast response in each measurement during the time period around 2-4 ms after the nearby stimulus. Mapping the relative amplitude of the neural response against the location of the respective recording electrode produces a neural sensitivity map of the neural tissue adjacent the electrode array. The neural sensitivity map so obtained by the present invention may be beneficial in several applications.

For example, the topographic map of sensitivity may be used to select the most sensitive electrodes for stimulation.

Sensing the neural compound action potential response, also referred to herein as the neural response, involves detection of the local field potential generated by the depolarisation of one or more axons along one or more nerve fibres. In some embodiments of the invention the evoked CAP measurements may be made by use of the neural response measurement techniques set out in the Australian provisional patent application No. 2011901817 in the name of National ICT Australia Ltd entitled "Method and apparatus for measurement of neural response" from which the present application claims priority. Additionally or alternatively, the neural response measurement may be conducted in accordance with any suitable CAP measurement technique.

Embodiments of the invention may provide for intraoperative monitoring of a neural sensitivity map. One such example is the surgical placement of percutaneous epidural electrodes. This procedure is typically performed under fluoroscopic examination in order to allow the physician to accurately place the electrode(s). The desired target location depends on the extent of coverage and the pain condition which is being treated, however in many circumstances the surgeon is aiming to place the electrode parallel with, and in line with the dorsal horn. Neural sensitivity mapping in accordance with the present invention can be used to aid electrode placement, as the evoked response amplitude is highest for an electrode substantially aligned with and parallel with dorsal horn. In this embodiment of the invention, surgical guidance is provided by a process in which the electrode is inserted in the vicinity of the target location, and pulse parameters of an applied neural stimulus are adjusted to establish a reliable evoked response measurement from the electrodes being implanted. The magnitude of the evoked response is repeatedly obtained to allow the neural sensitivity map to be monitored in real time as the electrode position is manipulated by the implanting surgeon. With such guidance the surgeon positions the electrode to achieve maximal response amplitude for a constant stimulation amplitude.

In this surgical process, the peak to peak amplitude of the evoked response can be displayed for the operating surgeon in a number of ways. A simple amplitude meter can be used or other graphical representation of the electrode location with respect to the spinal cord. The position can also be presented to the surgeon in an audible form with pitch and/or volume equating to the relative intensity of the evoked response.

In another embodiment, a neuromodulation system used for stimulation of peripheral nerves, for example the occipital nerve for the treatment of chronic migraine, is surgically positioned with the aid of the present invention. The evoked response arising from occipital stimuli applied by the implanted system is measured by sense electrodes, and used to help locate the position of the occipital nerve. The presence of an evoked response indicates the proximity of a nerve, and the strength of the evoked response can be used to intra-operatively fine tune the implant position.

Still another embodiment provides for an intra- or post-operative objective indication of the likely efficacy of spinal cord stimulation, prior to any user trial period. In such embodiments, the presence or absence of a strong Aβ response in the measurement of the evoked potential, and the diagnostic information from the neural properties, is used as an indication of the likely efficacy of spinal cord stimulation. Such embodiments may even eliminate the need to conduct trial stimulation periods. In such embodiments the procedure would be: (1) implant electrode array; (2) assess the quality of the neural sensitivity map and evoked responses, and (3) if acceptable responses are observed, the clinician can make the choice at this point to proceed to full implantation. Such embodiments recognise that the ability to measure the efficiency of Aβ fibre recruitment is directly related to the outcome of the therapy.

Figure 4:
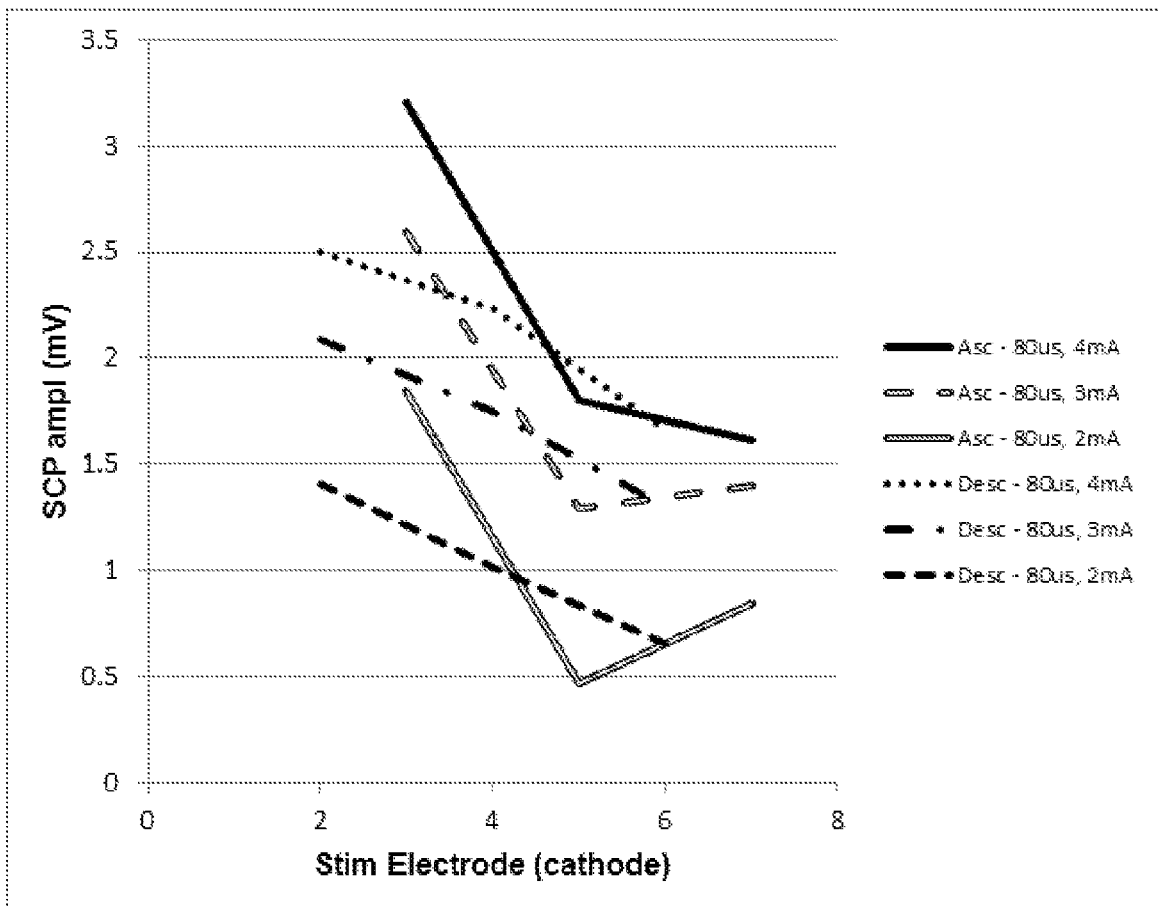
FIG. 4 illustrates the variation in evoked response amplitude with location along a vertebral segment.

In a further embodiment, the present invention is applied for electrode array location determination within a spinal segment. The spinal nerves join the spinal cord at each vertebral segment. The Aβ fibres enter the dorsal horn (dorsal horn entry zone) DREZ on the dorsal side, projecting from the dorsal root ganglia. The fibres cross the vertebrae in a bundle and then project up and down, sometimes as far as a few segments. The evoked response is proportional to the arrangement and distribution of fibres. FIG. 4 illustrates the variation in evoked response amplitude with location along a vertebral segment. The electrodes are positioned at 7 mm spacings along the array, giving a corresponding capability for position resolution. Thus, measurement of the evoked response map can be used to locate the electrode both laterally and caudorostrally with respect to a spinal segment, by referring to the modulation of the response along the electrode array arising from the variation in density of fibres. Thus, obtaining a neural sensitivity map in accordance with the present invention permits lateral and/or caudorostral implant positioning.

The relative intensities of the evoked response are related to both the separation of the electrode from the surface of the spinal cord and the properties of the fibres being stimulated. The effect of varying separation can be accounted for and so the intrinsic measure of the sensitivity of the spinal cord under each of the electrodes can be used to form a sensitivity map of the spinal cord.

Figure 5:
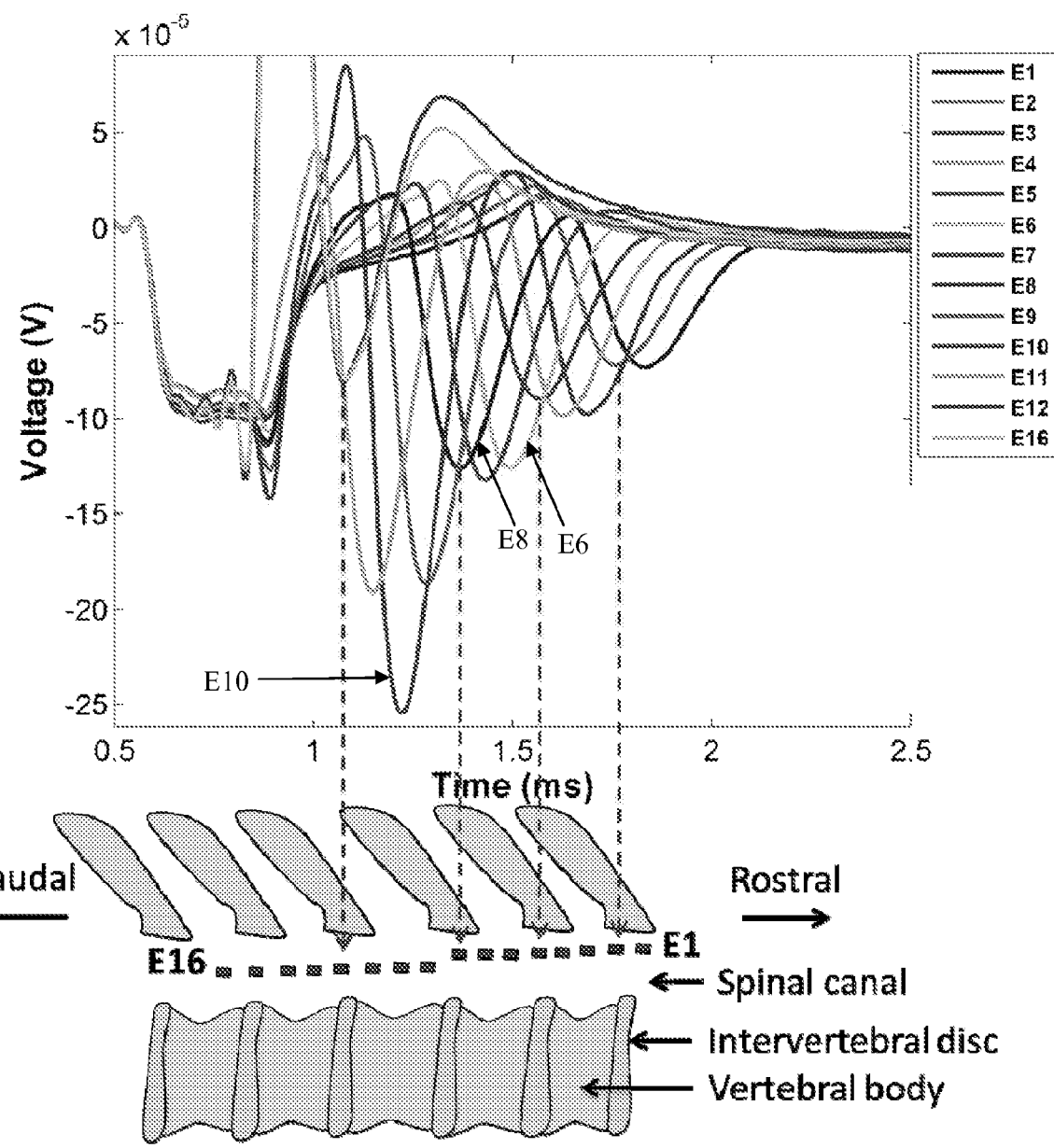
FIG. 5 illustrates the variation with location in sensed amplitude of measurements of a single evoked response from different electrodes positioned along a vertebral segment.

FIG. 5 illustrates the variation with location in sensed amplitude of measurements of a single evoked response from different electrodes positioned along a vertebral segment. As a single ECAP propagates along the dorsal columns, the recordings of distal electrodes contain the same tri-phasic morphology observed on the electrodes adjacent to the stimulus electrodes; only delayed in time, as a result of the conduction velocity, and with a variation in amplitude. The amplitude of the responses depends on the anatomical location of the recording electrode. This is illustrated in 5, where a stimulation current of 2.75 mA has been applied on electrodes 13-15, and the ECAP response as sensed at each other electrode is measured. In general, the electrodes positioned over the mid-vertebral segments (e.g. E10, E6), show larger measured potentials than do the electrodes positioned over the intervertebral discs (e.g., E8). The propagation direction is antidromic and a diagram indicating the anatomical placement of the electrodes is shown in the lower portion of FIG. 5. The envelope of the measured responses generally decays with increasing distance from the recording electrode however those electrodes located in the areas where there are intervertebral discs demonstrate a pronounced reduction in amplitude in comparison with their neighbors. This map profile is further illustrated in FIG. 7. Thus, a single stimulus enables a map to be obtained of the relative measurement sensitivity of all non-stimulating electrodes.

Figure 6:
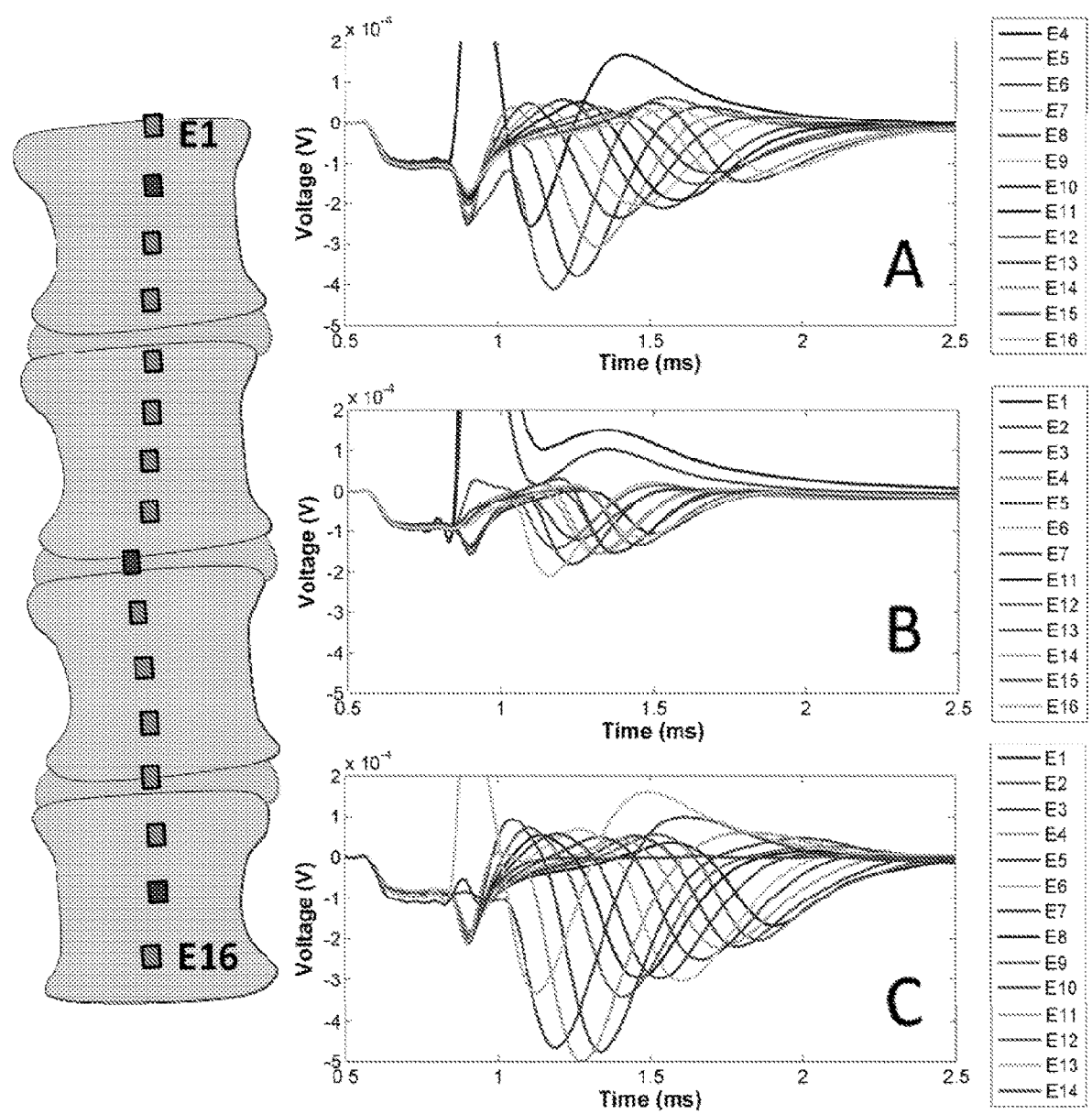
FIG. 6 illustrates the variation in actual amplitude of an evoked response, when applied by stimulus electrodes at different positions along a vertebral segment.

FIG. 6 illustrates the variation in actual amplitude of an evoked response, when applied by stimulus electrodes at different positions along a vertebral segment. Plot 6A shows measured responses when a stimulus is applied by the mid-vertebral electrode E2, plot 6B shows measured responses when the same stimulus is applied by the intervertebral electrode E9, and plot 6C shows measured responses when the same stimulus is applied by mid vertebral electrode E15. The amplitudes of the measurements of the neural response in plot B are less than half those of plots A and C, demonstrating the reduced neural recruitment ability of electrode E9 as compared to electrodes E2 and E15 because of its disadvantageous position. Mapping the array as shown in FIG. 5 permits such disadvantageously positioned electrodes to be identified and then omitted from a stimulus regime in order to maximise recruitment efficiency and conserve battery. In particular it is noted that similar variability in recruitment efficiency occurs with changes in lateral position relative to the dorsal column, so that optimising electrode position in both laterally and caudorostrally allows for power saving of up to a factor of perhaps 5 or 6, and may also improve device efficacy for patients who otherwise experience negligible or reduced benefit.

Figure 7A:
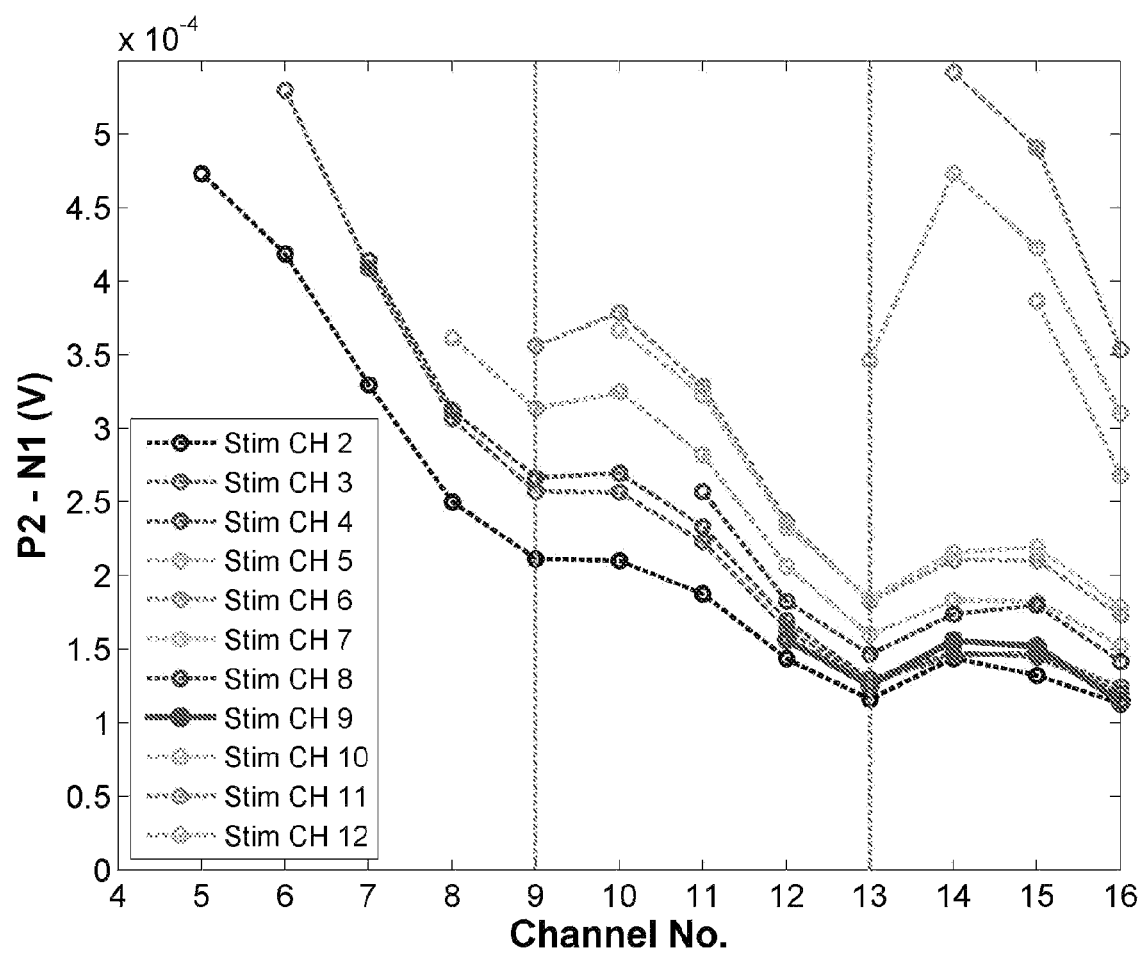
FIGS. 7a and 7b further illustrate caudorostral variations in electrode sensitivity and recruitment efficiency.
Figure 7B:
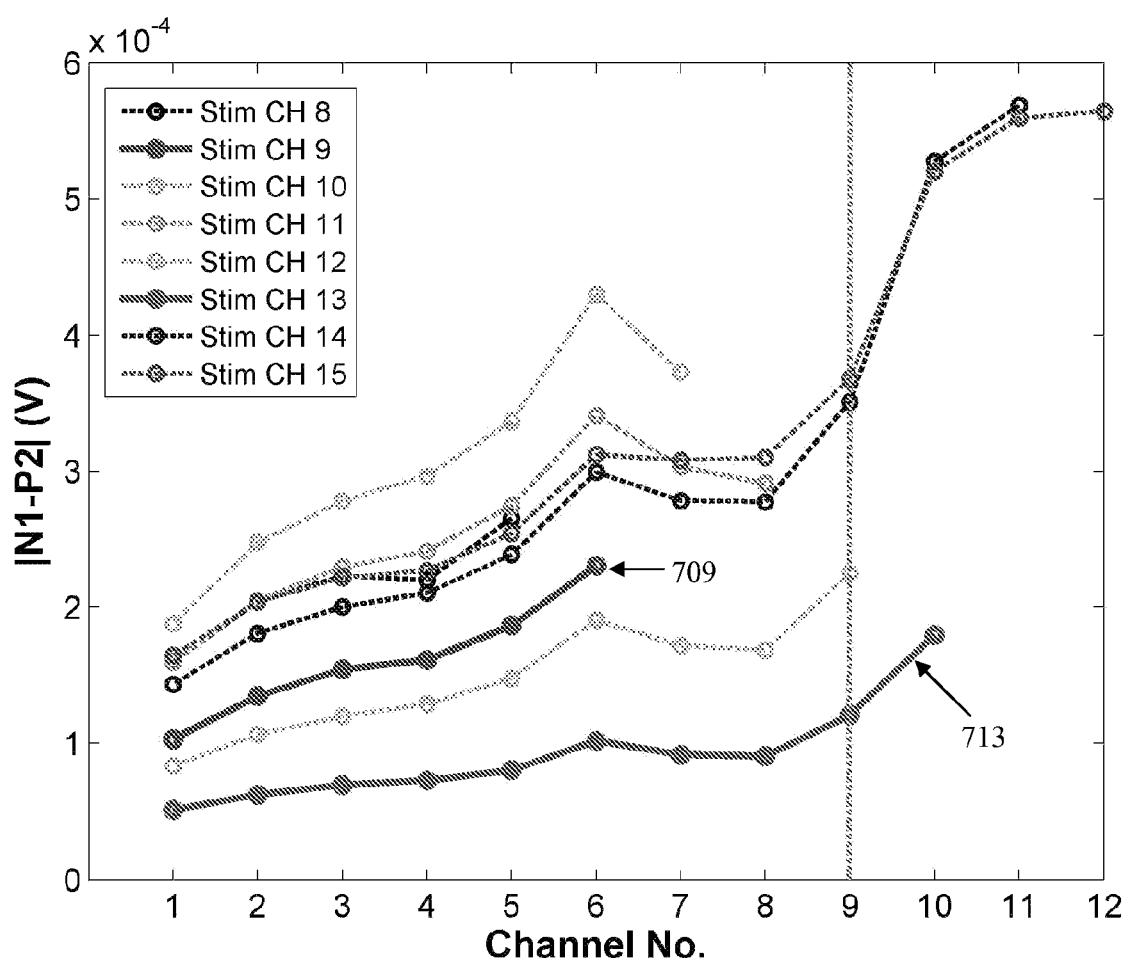

To further illustrate this phenomenon, the P2–N1 amplitude (at a fixed stimulation current, and pulse width of 40 μs) for all stimulation sites along the electrode array is presented in FIG. 7, in which orthodromic data (FIG. 7b) are separated from antidromic data (FIG. 7a) for all recording electrodes. Once again the amplitudes of the responses generally reduce with distance from the stimulation electrodes, but the responses at electrodes 13 and 9 in particular are further reduced from this trend line (FIG. 7a) due to their disadvantageous intervertebral position. Similarly, stimulation at electrodes 13 and 9 generated the weakest overall responses (responses 713 and 709, respectively, in FIG. 7b).

This embodiment of the invention thus recognizes that there are significant differences in the relative sensitivities of different areas along the spinal cord. The electrodes on which the lowest magnitude responses were recorded also generated the lowest evoked responses when used as the stimulating electrodes. This may be due to the separation between the electrode and the dorsal column fluctuating between the vertebrae as a natural consequence of the anatomy. The distance between the dorsal columns and the electrode is inversely proportional to its effectiveness. The increase in separation also reduces the response amplitude.

The amplitude and the excitability will also be affected by changes in the conductivity of the medium immediately surrounding the stimulating and recording electrode. Bone resistivity is more than twice that of the intervertebral discs that sit between the vertebral bodies and as a result the current spread from the stimulating electrodes in intervertebral positions would make recruitment less efficient and consequently smaller responses are observed.

Another possible explanation for the modulation in the response is due to the arrangement of the fibers within the dorsal columns. Each vertebra marks the introduction of new fibers from the corresponding dorsal roots. The excursion that these fibers take, as new laminae are laid down in the dorsal columns, will affect the position of fibers that entered the dorsal columns at lower segments. This will result in a change in the position of the fibers within the column and may manifest as a variation in the response amplitudes. Regardless of which reason(s) prove to be applicable, the present embodiment provides for a mapping of such variations and in turn the optimization of a stimulus program for the device as a whole. Noting that lead migration is a common problem in spinal cord stimulation, reassessing the "signature" response of the amplitude variation as shown in FIG. 7a could be used to determine the longitudinal change in the electrode position.

Figure 3:
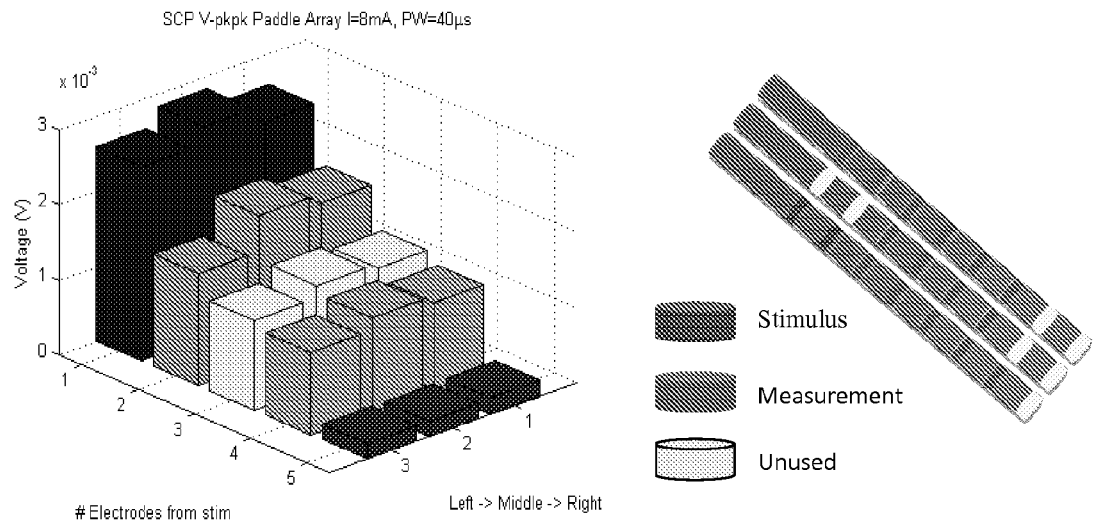
FIG. 3 illustrates the peak to peak amplitude of fast evoked responses measured by multiple electrodes of a paddle array.
Figure 8:
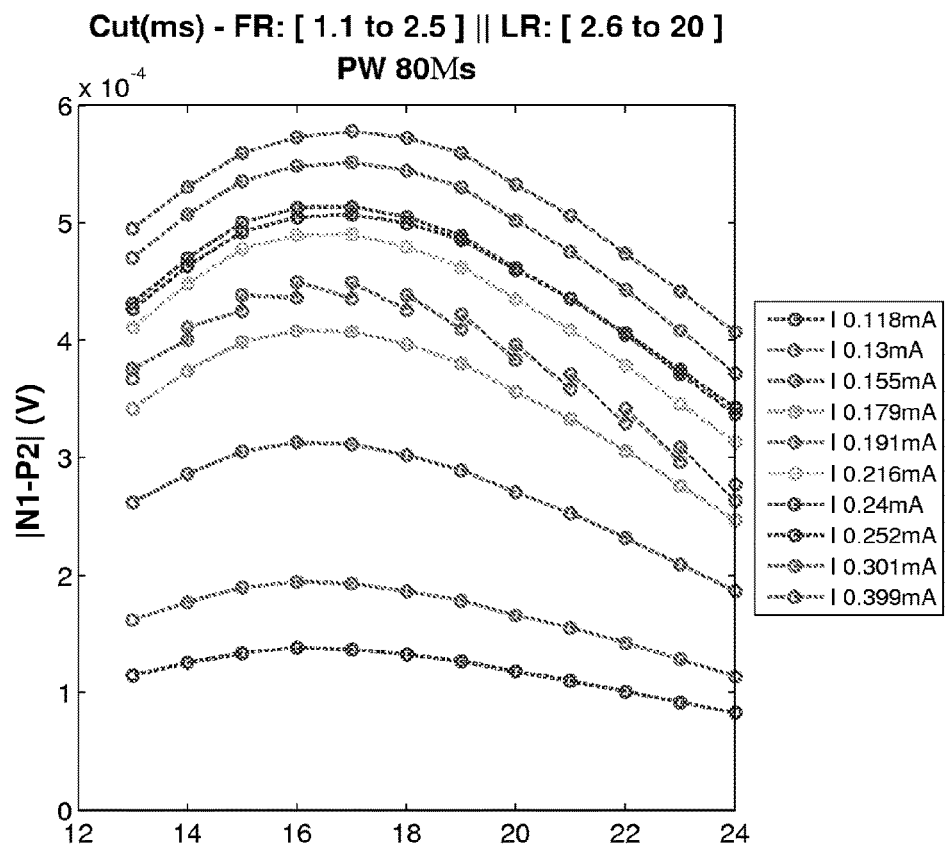
FIG. 8 illustrates the variation in evoked response amplitude with location across, laterally of, the dorsal column.

FIG. 8 illustrates the variation in evoked response amplitude with location across, i.e. laterally of, the dorsal column, and in particular plots the variation in amplitude (P2–N1) with the lateral electrode position. The sense electrode was positioned at a given distance laterally from the dorsal column, and used to sense evoked responses arising from a nearby applied stimulus. For each lateral position of the sense electrode, ten successive stimuli of varying amplitude were applied and sensed. FIG. 8 shows the measured N1–P2 data for 12 different lateral positions (nominated position numbers 13 through 24) of the sense electrode for stimuli of 10 different amplitudes. As can be seen the strength of the sensed response for a given stimulus is significantly stronger when the sense electrode is positioned in the centre of the dorsal column, at about position 17, and not laterally to either side. Delivery of stimuli from position 24 for example would consume significantly greater power to achieve the same therapeutic effect as compared to stimulating from position 17. Thus, this embodiment recognises that measurement of the evoked response map, with a suitable laterally configured array such as is shown in FIG. 1 or 3, can be used to locate a suitably located electrode laterally with respect to a spinal segment, by referring to the modulation of the response across the electrode array. Alternative embodiments may perform the mapping by applying the stimulus from varying lateral positions while sensing from a fixed reference position. Thus, obtaining a neural sensitivity map in accordance with the present invention permits lateral and/or caudorostral implant positioning and/or stimulus delivery.

In still further embodiments, the topographic neural sensitivity map may be used as a tool to monitor the function of the spinal cord to optimise surgical efficacy and minimise neurological side effects, in any one of a variety of surgical procedures. One such procedure is DREZ lesioning, which selectively destroys the dorsolateral aspect of the spinal cord at the area of entry of dorsal root fibres to the spinal cord, to produce a therapeutic benefit. DREZ is indicated for the control of medically refractory chronic pain associated with traumatic plexus avulsions. The lesions are made using one of a variety of techniques, including cutting with a surgical blade, through a series of radio frequent lesions, with a DREZ electrode, laser or focused ultrasound.

Figure 9:
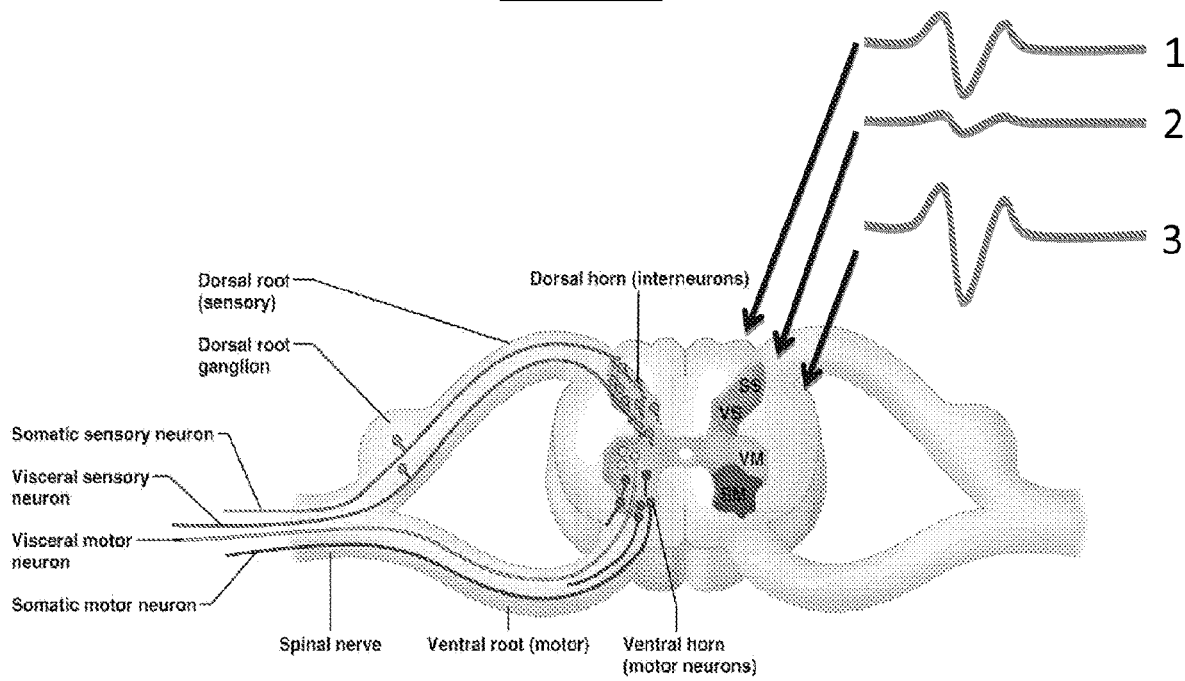
FIG. 9 illustrates measurements of spinal cord evoked potentials used for identifying the optimal site for DREZ lesioning.

This embodiment provides for a topographic neural sensitivity map to be obtained from simultaneous measurements of a single evoked neural response, to provide a guide as to the best location to perform the lesion. FIG. 9 illustrates spinal cord evoked potentials and their use in identifying the optimal site for DREZ lesioning. In particular, by applying stimulation at different sites around the DREZ (locations 1 and 3 in FIG. 9) produced neural responses. In contrast stimulation at the DREZ (location 2) provoked only weak responses. The site for DREZ lesioning was identified as corresponding to the site at which no response to stimulation was evoked. The evoked response can be recorded repeatedly or continuously over the region of the spinal cord lesion with for instance a paddle array of electrodes. A neurophysiological response map of the spinal cord can be made by stimulation and recording on combinations of electrodes. For instance the dead region (area where there is a significantly low response over the spinal cord) can be determined by scanning the entire array of electrodes with a stimulus pulse and recording for all other electrodes (or nearest neighbour). A map of the low response region can then be directly visualised from the response map.

A further enhancement enabled by this embodiment of the invention involves, after obtaining the required topographic neural sensitivity map and satisfactorily locating the target lesioning site, connecting the recording electrodes to radiofrequency (RF) ablation equipment via a switching mechanism so that the system can automatically select the electrodes closest to the target lesioning site, and use those electrodes to apply the RF lesioning burst. Incremental lesioning may further be undertaken, with the neural mapping exercise being carried out on an iterative basis so that the extent of lesioning can be more finely controlled.

As will be appreciated, the technique of this embodiment is not restricted to the use of RF lesioning but can use other forms of tissue removal, for example laser ablation. As discussed previously herein, the measurement of a map of the locally excited ECAP provides a great deal of information about the fibre properties. This information can be used in any surgical setting where it is desirable to isolate one type of fibre group (with distinct properties) from others for selective treatment e.g. by deaxonation. Fine control could be exercised with laser surgery.

In yet another embodiment of the invention, continuous recording is performed of evoked responses. The evoked responses can be generated either by electrical stimulation of the spinal cord or by electrical or mechanical stimulation at the periphery. This can be used to aid finding the ideal location for electrical stimulation to produce the optimal therapeutic effect. The procedure would be as follows:

1. TENS electrodes or a mechanical stimulator is placed over the painful area.
2. The spinal cord stimulation electrode array is placed in the epidural space.
3. The Evoked Responses are recorded for each electrode, as illustrated in FIG. 2, to obtain the neural sensitivity map.
4. The stimulation site is selected by reference to the electrode which measured a target feature. For example the target feature may be the largest response amplitude, and the stimulation site location may be chosen to be at that measurement site or at a site derived by reference to the measurement site.

To improve the signal to noise ratio the evoked response measurements are averaged over a number of recording cycles. In order to perform the averaging the stimulus is a periodically varying signal, with stimulus position in time known for each stimulus to enable the averaging procedure. During inter-operative placement the stimulus can be generated by an external stimulator which is interfaced directly with the response measurement amplifier to synchronise the timing of the measurements with the stimulus.

Figure 10:
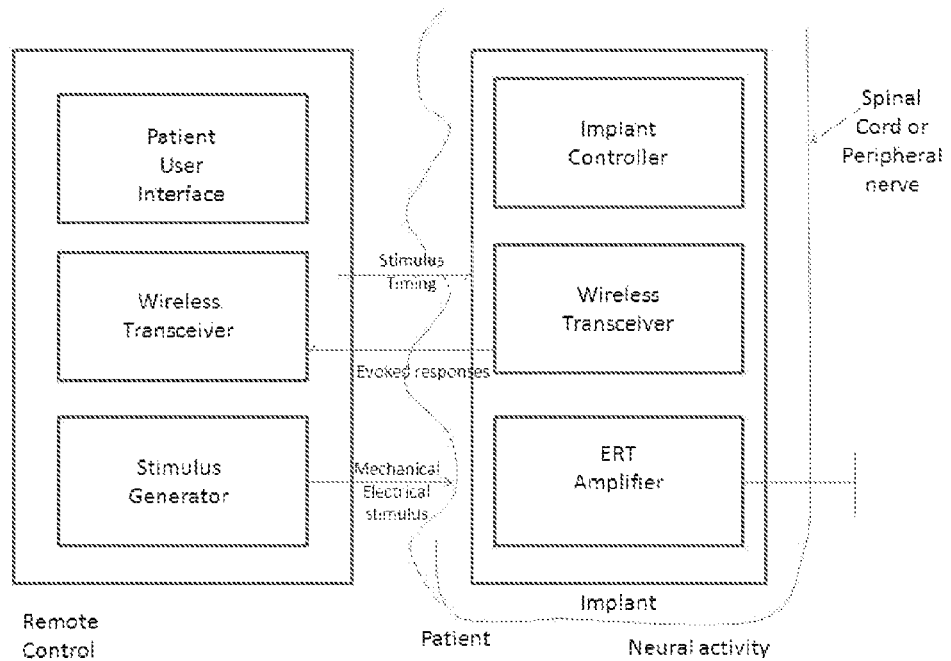
FIG. 10 is a block diagram of a system incorporating an implant remote control configured for generating TENS or mechanical stimuli.

Thus some embodiments of the invention provide for stimulation at the periphery to locate the best locus of neural excitation. The common surgical procedure for implantation of percutaneous spinal cord leads involves a process referred to as trawling. The electrode is placed at a higher position than required as predicted by the dermatome map and then the electrode is slowly moved (pulled back) while stimulating until the conscious patient reports a correspondence between the area of paraesthesia and pain. Evoked response measurements can be used to locate the ideal area of stimulation by applying a stimulus over the area which is painful by suitable means (e.g. a TENS apparatus) and then determination of the electrode which measures the largest evoked response. The peripheral stimulation provides a means to identify the best location for the electrode placement and doesn't rely on feedback from the patient. The patient can be in a general anesthetised state (or otherwise incapable of communicating feedback), which may be desirable under some circumstances In some embodiments the method of the present invention is configured for operation after the time of initial implantation of the electrode, as well as for intra-operative determination of the location for stimulation. For post-operative neural mapping, a spinal cord system is used in conjunction with a remote control (FIG. 10) to control the location of the stimulation. The remote control communicates with the implant via wireless communication. Various means may be used to allow this communication to be done efficiently (e.g. by reducing the number of times the communication link is polled depending on the activity of the system). The patient remote control provides a means to operate or change parameters stored in the implant so that the user has the ability to adjust the stimulus to achieve an optimal therapeutic outcome regardless of changing circumstances.

Lead migration represents a major issue for spinal cord stimulators Lead movement can result in changes to stimulation parameters or location having to be made to achieve optimal pain relief. This may not be due to a change in the required therapeutic location on the spinal cord, but rather because the lead has moved relative to its original location. Thus, in this embodiment adjustment of stimulus location can be made by selecting alternative programs with the remote control. Alternatively the above mentioned technique may be used by placing TENS pads or a mechanical stimulator over the painful site and using the amplitude of the evoked response to locate the new desired site for stimulation. Further the TENS or mechanical stimulator may be incorporated in the remote control unit, the remote control unit ideally being a hand held device which when placed against the skin over the painful area, provides a TENS stimulus which induces an evoked response which can be detected in the spinal cord to provide the necessary neural map.

Figure 11:
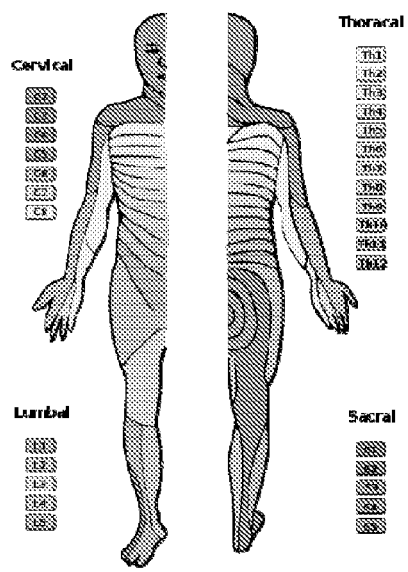
FIG. 11 illustrates a map of the dermatomes in a human body.

One difficulty faced in programming any neuro-modulation system is to determine the locus of stimulation on a perceptual body map. This is because, in existing systems, there is no way to standardise the stimulus such that it produces a constant level of recruitment. Varying the stimulus amplitude has an effect on both the locus of the perceived stimulation and on the area covered. Stimulating at fixed point above threshold ($n \cdot T_e$) for the A$\beta$ fibres allows stimulation at fixed level of recruitment. Thus, one embodiment of the invention provides for measurement of stimulus threshold over multiple electrodes in order to create a percept body map. The stimulation threshold for neural recruitment can be determined from the peak to peak amplitudes of the fast response. It corresponds to the minimum stimulation level required to produce a psycho-physical sensation. An accurate body map relating percept with electrode stimulation location can be determined by stimulating each electrode in turn and asking the patient to locate the locus of perception on a graphical body map (such as shown in FIG. 11). The dermatomes shown are each an area of perception on the skin innervated by a single spinal nerve, and thus relate these areas to the corresponding level where they enter the spinal cord. A body map based on threshold or other constant recruitment condition provides a means to select electrodes to achieve the desired level of coverage. The thresholds can be determined for single electrodes as stimulating sites, or for two electrodes used in parallel as a single site, or any other combination of electrodes.

The task of the clinician programming the system is to optimise the pain relief through selecting stimulus parameters and location to achieve coverage (matching the area of paraesthesia with area over which the patient experiences pain). The choice between stimulating at one or two locations can have an impact on the power consumption of the system. Mapping the percepts at constant A$\beta$ evoked responses allows the clinician and user to quickly identify electrodes which are aligned with the regions required for pain relief. The differences in percept for different combinations of electrodes provides a guide for lowering power consumption. For example, where two electrodes correspond to the same paraesthesia location, then stimulation on those two together will reduce the power consumption of the device.

Still further embodiments of the invention may provide for the neural sensitivity map to serve as a diagnostic tool. Routinely, during assessment of patients for spinal cord stimulation therapy, the patient will undergo a trial stimulation procedure. This is where the patient is implanted with a percutaneous lead with an externalised set of contacts. The lead is attached to an external pulse generator and the patient has use of the device for several days. At the end of the trial period the clinician and patient assess the performance of the system with regard to pain relief and a choice is made whether or not to proceed with a full implantation. In this embodiment of the invention, the take-home device for trial purposes may consist of both a stimulus generator but also an evoked response measurement and mapping system. The ERT response maps recorded during the trial period could be used to adjust the stimulus parameters as described above.

The neural response measurement system of some embodiments of this invention may measure amplitude growth functions etc., collected at the time of surgery and also during the trial stimulation period which, together with subjective performance measures, could be used to develop a correlation between the response parameters and the patient outcomes. For instance, there is considerable variation between patients in threshold response, and there may exist a correlation between threshold and outcome, where lower thresholds generate better outcomes. There are a large number of neurological parameters that can be collected in performing neural map measures, including amplitude response, conduction velocity, refractory periods etc. Systematic collection of this data across a number of patients will allow analysis for correlation with outcome.

The intra-operative measurement system may in turn be equipped with algorithms based on the analysis of past surgeries, trial periods and patient responses, to inform the clinician at the time of a new surgery as to the likelihood of a favourable patient outcome. The clinician may then be given a choice whether to proceed with the full implant procedure at this time. One special case is if the system records no responses at all which indicates that any patient benefit is unlikely.

The neurophysiological properties of the spinal cord measured from the epidural space may be important in a number of other diagnostic situations in which the present invention may be applied. For example it may be desirable to monitor the condition of the spinal cord during recovery from back surgery or after back injury.

There are several techniques which are routinely performed in order to optimally place an electrode during surgery. The procedure is generally to determine the site for the electrode to be introduced by selecting a vertebral level, based on the area of perception of the pain. The vertebral level is determined from a dermatome map. The surgeon then places the electrode (under fluoroscopy for a percutaneous introduced electrode array) at the vertebral level corresponding to the identified dermatome. For paddle style electrodes the array is introduced after a laminectomy is performed.

Some electrodes are more sensitive than others due to their proximity to a higher density of Aβ fibres in the DREZ, a fact illustrated in FIGS. 4 and 8. Anecdotal data from sheep experiments, as well as a consideration of spinal cord anatomy, suggests that as the epidural stimulation site shifts laterally from the midline, the chance of eliciting motor reflexes and other responses of the motor neurons increases. For a given stimulus intensity, if the slow responses appear or become larger than previously, this is an indicator that lateral movement of the electrode has occurred. Further, if the ratio of the slow response to fast response thresholds changes, this may also indicate lateral migration. This scenario may lead to undesired sensation and may need to be rectified. Accordingly, in some embodiments in which a paddle electrode is used, the stimulation electrodes may be changed to electrodes which are medial to the current (off-centre) stimulating electrodes. If a single "percutaneous" electrode array is used, the stimulus intensity may be reduced to avoid the undesired sensation produced, or again the stimulus location may be shifted. Both of these changes could be made in an automated fashion with a feedback controller, based on neural sensitivity maps obtained in accordance with the present invention.

In another embodiment the present invention may be applied in relation to dorsal root ganglion (DRG) stimulation and measurement in the spinal cord Direct stimulation of the DRG has been shown to be effective in paraesthesia generation and pain relief for individuals suffering from chronic pain. Accessing the DRG requires design of specific stimulation electrodes such as a hook electrode. DRG stimulation is designed to recruit the Aβ fibres present on the outer surface of the DRG. The large diameter fibres, which are more easily stimulated, partition to the outside of the DRG and these are mainly Aβ. The foramen where the DRG sits is more confined than the epidural space where an electrode is placed for epidural stimulation of the spinal cord. Because of this confinement, fixed stimulation parameters tend to provide a more stable paraesthesia sensation in DRG stimulation as compared to epidural stimulation. The DRG electrodes are programmed via a standard neuromodulation stimulation paradigm in which location and size of paraesthesia are adjusted via stimulation parameters to generate paraesthesias which overlap the painful area. This embodiment recognises that evoked response measurement in accordance with the present invention can be used to optimize the response from DRG electrode systems similarly as described for other embodiments in the preceding. Such measurements permit optimization of stimulation parameters, optimization of dynamic neural responses and closed loop feedback control to eliminate variations in delivered therapy. Both sense and stimulus electrodes can be placed directly in the DRG. Alternatively, stimulus electrodes can be placed in the DRG and recordings can be made from the spinal columns with electrodes placed in the epidural space.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A method for determining a desired location at which to apply a neural therapy, the method comprising:
implanting an array of electrodes mounted on a common paddle proximal to neural tissue, where a first plurality of electrodes in the array are configured to provide an electrical stimulus, and a second plurality of electrodes in the array are configured to internally measure neural compound action potential responses;
applying a stimulus from the array which evokes a neural compound action potential response in the neural tissue proximal to the array using the first plurality of electrodes;
obtaining a plurality of simultaneous respective internal measurements of the neural compound action potential response evoked by applying the stimulus using the second plurality of electrodes, the plurality of simultaneous respective internal measurements being obtained from respective distinct measurement amplifiers each connected to respective distinct electrodes of the second plurality of electrodes; and
determining from the plurality of internal measurements of the neural compound action potential response a neural sensitivity map of the area alongside the array and determining therefrom a desired location at which to apply a neural therapy.

2. The method of claim 1, wherein the array comprises a large number of electrodes configured to obtain a plurality of simultaneous internal measurements of a neural response, in order to yield fine spatial resolution of the neural sensitivity map of the area alongside the array.

3. The method of claim 2, wherein the array comprises 24 electrodes arranged in 3 columns and 8 rows.

4. The method of claim 1, further comprising providing intra-operative information regarding the neural response.

5. The method of claim 4, further comprising generating a neural sensitivity map around the DREZ in order to guide DREZ lesioning, wherein the neural sensitivity map is generated intra-operatively.

6. The method of claim 5, further comprising performing DREZ lesioning in progressive increments, iteratively with neural sensitivity mapping, whereby the ongoing neural sensitivity mapping provides a progressive intra-operative gauge of the effects of lesioning.

7. The method of claim 5, wherein the DREZ lesioning is performed by RF ablation, applied from the same electrode array as is used for the sensitivity mapping.

8. The method of claim 1, further comprising generating a sensitivity map based upon the plurality of internal measurements, and optimizing the position of an electrode or electrode array being implanted using the sensitivity map, wherein the sensitivity map is generated intra-operatively.

9. The method of claim 8, further comprising positioning the electrode array laterally relative to the spinal cord.

10. The method of claim 8, further comprising positioning the electrode array caudorostrally relative to the spinal cord.

11. The method of claim 1, further comprising providing intra-operative information representing the plurality of internal measurements of the neural compound action potential response to a surgeon using an amplitude meter.

12. The method of claim 1, further comprising giving ongoing post-operative guidance as to the suitability of the site of the neural therapy.

13. The method of claim 12, further comprising determining when manual or automated re-fitting of a therapeutic device is required, to cause a site of the neural therapy to be revised in response to the ongoing measurements.

14. The method of claim 1, wherein a selection of which electrode(s) to use to apply a therapeutic stimulus is post-operatively altered in response to a map of neural sensitivity as measured at each electrode.

15. The method of claim 1, wherein the stimulus is applied under the control of a remote control of the implanted array.

16. The method of claim 1, wherein the first plurality of electrodes and the second plurality of electrodes share at least one electrode.

17. A system for determining a desired location at which to apply a neural therapy, the system comprising:
   an array of electrodes mounted on a common paddle implanted into a patient configured to be positioned proximal to neural tissue, the array comprising:
      a first plurality of electrodes configured to provide an electrical stimulus, and
      a second plurality of electrodes configured to measure neural compound action potential responses;
   a plurality of measurement amplifiers each connected to a respective electrode of the second plurality of electrodes;
   a control unit configured to cause application of a stimulus from the array which evokes a neural compound action potential response in the neural tissue proximal to the array using the first plurality of electrodes, the control unit further configured to simultaneously obtain a plurality of respective internal measurements of the neural compound action potential response from a plurality of electrodes of the array using the second plurality of electrodes, the plurality of simultaneous respective internal measurements being obtained from the respective distinct measurement amplifiers each connected to respective distinct electrodes of the second plurality of electrodes, and the control unit further configured to determine from the plurality of internal measurements of the neural compound action potential response a neural sensitivity map of the area alongside the array and to determine therefrom a desired location at which to apply a neural therapy.

18. The system of claim 17, wherein the first plurality of electrodes and the second plurality of electrodes share at least one electrode.

* * * * *